US012637688B2

(12) United States Patent
Min et al.

(10) Patent No.: US 12,637,688 B2
(45) Date of Patent: May 26, 2026

(54) DNA CONSTRUCT FOR DIAGNOSING AND TREATING CANCER

(71) Applicant: CNCURE BIOTECH INC., Hwasun-eup (KR)

(72) Inventors: Jung Joon Min, Gwangju (KR); Hyon El Choy, Seoul (KR); Yeong Jin Hong, Gwangju (KR); Sung Hwan You, Gwangju (KR); Mi Ryung Song, Yongin-si (KR)

( * ) Notice: Subject to any disclaimer, the term of this patent is extended or adjusted under 35 U.S.C. 154(b) by 824 days.

(21) Appl. No.: 17/610,086

(22) PCT Filed: May 11, 2020

(86) PCT No.: PCT/KR2020/006197
§ 371 (c)(1),
(2) Date: Nov. 9, 2021

(87) PCT Pub. No.: WO2020/231137
PCT Pub. Date: Nov. 19, 2020

(65) Prior Publication Data
US 2022/0228165 A1     Jul. 21, 2022

(30) Foreign Application Priority Data

May 10, 2019     (KR) ........................ 10-2019-0055063
May 11, 2020     (KR) ........................ 10-2020-0056115

(51) Int. Cl.
*C12N 15/85*          (2006.01)
*A61K 48/00*          (2006.01)
*A61P 35/00*          (2006.01)
*C12N 15/65*          (2006.01)
*C12N 15/74*          (2006.01)

(52) U.S. Cl.
CPC ............ *C12N 15/85* (2013.01); *A61K 48/005* (2013.01); *A61P 35/00* (2018.01); *C12N 15/65* (2013.01); *C12N 15/74* (2013.01); *C12N 2830/003* (2013.01)

(58) Field of Classification Search
CPC ........ C12N 15/85; C12N 15/65; C12N 15/74; C12N 2830/003; C12N 2830/002; A61K 48/005; A61K 49/18; A61P 35/00; A01K 2207/12; A01K 2227/105; A01K 2267/0331; Y02A 50/30; C12Q 1/66
See application file for complete search history.

(56) References Cited

U.S. PATENT DOCUMENTS

| | | | |
|---|---|---|---|
| 10,131,915 B2 | 11/2018 | Roth et al. | |
| 2002/0061528 A1 | 5/2002 | Gardner et al. | |
| 2004/0224412 A1 | 11/2004 | Hannoufa et al. | |
| 2014/0107190 A1* | 4/2014 | Martin Molina ...... | C12N 15/86 |
| | | | 435/375 |
| 2017/0137831 A1* | 5/2017 | Roth ........................ | C12N 1/20 |
| 2020/0277592 A1* | 9/2020 | Boisart .................... | C12N 9/18 |

OTHER PUBLICATIONS

Jiang et al. "Engineering of bacteria for the visualization of targeted delivery of a cytolytic anticancer agent." Molecular Therapy 21.11 (2013): 1985-1995 (Year: 2013).*

Jiang et al., "Engineering of Bacteria for the Visualization of Targeted Delivery of a Cytolytic Anticancer Agent," Molecular Therapy, 21(11):1985-1995 (2013).

Hong et al., "TetR repressor-based bioreporters for the detection of doxycycline using *Escherichia coli* and Acinetobacter oleivorans," Applied Microbiology and Biotechnology, 98(11):5039-5050 (2014).

Liang et al., "Genetically engineered *Salmonella typhimurium*: Recent advances in cancer therapy," Cancer Letters, 448:168-181 (2019).

Nguyen et al., "Optimized Doxycycline-Inducible Gene Expression System for Genetic Programming of Tumor-Targeting Bacteria," Molecular Imaging and biology, 24:82-92 (2022).

Baron et al., "Co-regulation of two gene activities by tetracycline via a bidirectional promoter," Nucleic Acids Research, 23(17):3605-3606 (1995).

Li-Juan Wang, et al., "Engineering Halomonas bluephagenesis via small regulatory RNAs", Metabolic Engineering, 73 (2022), pp. 58-69.

Georgi, et al. "Promoter strength driving TetR determines the regulatory properties of Tet-controlled expression systems." PLoS One. 2021, vol. 7, No. 7, p. 1-15.

Bertram, et al. "The application of Tet repressor in prokaryotic gene regulation and expression." Microbial Biotechnology. 2008, vol. 1, No. 1, p. 2-16.

International Search Report and Written Opinion of International Application PCT/KR2020/006197 dated Aug. 31, 2020.

(Continued)

*Primary Examiner* — Alexander W Nicol
(74) *Attorney, Agent, or Firm* — McDonnell Boehnen Hulbert & Berghoff LLP

(57) ABSTRACT

The present disclosure relates to a DNA construct, and a strain into which a recombinant vector comprising the DNA construct has been introduced. The DNA construct according to the present disclosure allows the expression levels of genes, operably linked downstream of first and second promoters, in a host strain or cell, to be balanced, so that cancer diagnosis and treatment may be performed simultaneously. In addition, the DNA construct of the present disclosure completely does not allow the anticancer protein and the reporter protein to be expressed at all in the absence of doxycycline, and thus it allows the anticancer protein to be expressed at an appropriate dose for cancer treatment by controlling whether or not treatment with doxycycline is performed, and at the same time, enables the size of the cancer to be monitored in real time depending on the expression level of the reporter protein.

15 Claims, 16 Drawing Sheets
Specification includes a Sequence Listing.

(56) References Cited

OTHER PUBLICATIONS

Part:BBa_J23113, Registry of Standard Biological Parts, iGem, https://parts.igem.org/Part:BBa_J23113.

* cited by examiner

[FIG. 12]

$P_{tetA}::clyA, P_{tetR}::Rluc8$
(pJH18-CR)

SEQUENCE LISTING

<160> NUMBER OF SEQ ID NOS: 16

<210> SEQ ID NO 1
<211> LENGTH: 305
<212> TYPE: PRT
<213> ORGANISM: Homo sapiens

<400> SEQUENCE: 1

Met Ile Met Thr Gly Ile Phe Ala Glu Gln Thr Val Glu Val Val Lys
1               5                   10                  15

Ser Ala Ile Glu Thr Ala Asp Gly Ala Leu Asp Leu Tyr Asn Lys Tyr
            20                  25                  30

Leu Asp Gln Val Ile Pro Trp Lys Thr Phe Asp Glu Thr Ile Lys Glu
        35                  40                  45

Leu Ser Arg Phe Lys Gln Glu Tyr Ser Gln Glu Ala Ser Val Leu Val
    50                  55                  60

Gly Asp Ile Lys Val Leu Leu Met Asp Ser Gln Asp Lys Tyr Phe Glu
65                  70                  75                  80

Ala Thr Gln Thr Val Tyr Glu Trp Cys Gly Val Val Thr Gln Leu Leu
                85                  90                  95

Ser Ala Tyr Ile Leu Leu Phe Asp Glu Tyr Asn Glu Lys Lys Ala Ser
            100                 105                 110

Ala Gln Lys Asp Ile Leu Ile Arg Ile Leu Asp Asp Gly Val Lys Lys
        115                 120                 125

Leu Asn Glu Ala Gln Lys Ser Leu Leu Thr Ser Ser Gln Ser Phe Asn
    130                 135                 140

Asn Ala Ser Gly Lys Leu Leu Ala Leu Asp Ser Gln Leu Thr Asn Asp
145                 150                 155                 160

Phe Ser Glu Lys Ser Ser Tyr Phe Gln Ser Gln Val Asp Arg Ile Arg

```
              165                   170                   175
Lys Glu Ala Tyr Ala Gly Ala Ala Ala Gly Ile Val Ala Gly Pro Phe
              180                   185                   190
Gly Leu Ile Ile Ser Tyr Ser Ile Ala Ala Gly Val Ile Glu Gly Lys
          195                   200                   205
Leu Ile Pro Glu Leu Asn Asn Arg Leu Lys Thr Val Gln Asn Phe Phe
      210                   215                   220
Thr Ser Leu Ser Ala Thr Val Lys Gln Ala Asn Lys Asp Ile Asp Ala
225                   230                   235                   240
Ala Lys Leu Lys Leu Ala Thr Glu Ile Ala Ala Ile Gly Glu Ile Lys
              245                   250                   255
Thr Glu Thr Glu Thr Thr Arg Phe Tyr Val Asp Tyr Asp Asp Leu Met
              260                   265                   270
Leu Ser Leu Leu Lys Gly Ala Ala Lys Lys Met Ile Asn Thr Cys Asn
          275                   280                   285
Glu Tyr Gln Gln Arg His Gly Lys Lys Thr Leu Phe Glu Val Pro Asp
      290                   295                   300
Val
305
```

```
<210> SEQ ID NO 2
<211> LENGTH: 46
<212> TYPE: DNA
<213> ORGANISM: Artificial Sequence
<220> FEATURE:
<223> OTHER INFORMATION: Forward primer

<400> SEQUENCE: 2
cggaattcac catgtctaga ttagataaaa gtaaagtgat taacag                     46

<210> SEQ ID NO 3
<211> LENGTH: 48
<212> TYPE: DNA
<213> ORGANISM: Artificial Sequence
<220> FEATURE:
<223> OTHER INFORMATION: Reverse primer

<400> SEQUENCE: 3
gctctagaca gctgttaaga cccactttca catttaagtt gttttttct                  48

<210> SEQ ID NO 4
<211> LENGTH: 39
<212> TYPE: DNA
<213> ORGANISM: Artificial Sequence
<220> FEATURE:
<223> OTHER INFORMATION: Forward primer

<400> SEQUENCE: 4
ctactccgtc aagccgtcaa gctgttgtga ccgcttgct                             39

<210> SEQ ID NO 5
<211> LENGTH: 57
<212> TYPE: DNA
<213> ORGANISM: Artificial Sequence
<220> FEATURE:
<223> OTHER INFORMATION: Reverse primer

<400> SEQUENCE: 5
tgaattcctc ctgctagcta gttggtaacg aatcagacgc cgggtaatac cggatag        57

<210> SEQ ID NO 6
```

<211> LENGTH: 39
<212> TYPE: DNA
<213> ORGANISM: Artificial Sequence
<220> FEATURE:
<223> OTHER INFORMATION: Forward primer

<400> SEQUENCE: 6
tgctactccg tcaagccgtc aagctgttgt gaccgcttg                                      39

<210> SEQ ID NO 7
<211> LENGTH: 39
<212> TYPE: DNA
<213> ORGANISM: Artificial Sequence
<220> FEATURE:
<223> OTHER INFORMATION: Reverse primer

<400> SEQUENCE: 7
agcttggtaa cgaatcagac gccgggtaat accggatag                                      39

<210> SEQ ID NO 8
<211> LENGTH: 6
<212> TYPE: DNA
<213> ORGANISM: Artificial Sequence
<220> FEATURE:
<223> OTHER INFORMATION: -35 promoter sequence

<400> SEQUENCE: 8 ttcgcg                                                                           6

<210> SEQ ID NO 9
<211> LENGTH: 9
<212> TYPE: DNA
<213> ORGANISM: Artificial Sequence
<220> FEATURE:
<223> OTHER INFORMATION: -10 promoter sequence

<400> SEQUENCE: 9 atgcataat                                                                        9

<210> SEQ ID NO 10
<211> LENGTH: 78
<212> TYPE: DNA
<213> ORGANISM: Artificial Sequence
<220> FEATURE:
<223> OTHER INFORMATION: Forward primer

<400> SEQUENCE: 10
ccctatgcta ctccgtcaag ccgtcaattg ttgacaatta atcatcggct cgtataatgt            60
ctgattcgtt accaagct                                                          78

<210> SEQ ID NO 11
<211> LENGTH: 78
<212> TYPE: DNA
<213> ORGANISM: Artificial Sequence
<220> FEATURE:
<223> OTHER INFORMATION: Reverse primer

<400> SEQUENCE: 11
agcttggtaa cgaatcagac attatacgag ccgatgatta attgtcaaca attgacggct            60
tgacggagta gcataggg                                                          78

<210> SEQ ID NO 12
<211> LENGTH: 75
<212> TYPE: DNA
<213> ORGANISM: Artificial Sequence -continued

```
<220> FEATURE:
<223> OTHER INFORMATION: Forward primer

<400> SEQUENCE: 12
tgctactccg tcaagccgtc tttacagcta gctcagtcct aggtataatg ctagccaatt      60
gtctgattcg ttacc                                                      75

<210> SEQ ID NO 13
<211> LENGTH: 75
<212> TYPE: DNA
<213> ORGANISM: Artificial Sequence
<220> FEATURE:
<223> OTHER INFORMATION: Reverse primer

<400> SEQUENCE: 13
ggtaacgaat cagacaattg gctagcatta tacctaggac tgagctagct gtaaagacgg      60
cttgacggag tagca                                                      75

<210> SEQ ID NO 14
<211> LENGTH: 75
<212> TYPE: DNA
<213> ORGANISM: Artificial Sequence
<220> FEATURE:
<223> OTHER INFORMATION: Forward primer

<400> SEQUENCE: 14
tgctactccg tcaagccgtc ttgacagcta gctcagtcct aggtataatg ctagccaatt      60
gtctgattcg ttacc                                                      75

<210> SEQ ID NO 15
<211> LENGTH: 75
<212> TYPE: DNA
<213> ORGANISM: Artificial Sequence
<220> FEATURE:
<223> OTHER INFORMATION: Reverse primer

<400> SEQUENCE: 15
ggtaacgaat cagacaattg gctagcatta tacctaggac tgagctagct gtcaagacgg      60
cttgacggag tagca                                                      75

<210> SEQ ID NO 16
<211> LENGTH: 192
<212> TYPE: DNA
<213> ORGANISM: Unknown
<220> FEATURE:
<223> OTHER INFORMATION: OXB1 promoter

<400> SEQUENCE: 16
aagctgttgt gaccgcttgc tctagccagc tatcgagttg tgaaccgatc catctagcaa      60
ttggtctcga tctagcgata ggcttcgatc tagctatgta gaaacgccgt gtgctcgatc     120
gcctgacgct ttttatcgca actctctact gttgcttcaa cagaacatat tgactatccg     180
gtattacccg gc                                                        192
```

DNA CONSTRUCT FOR DIAGNOSING AND TREATING CANCER

CROSS-REFERENCE TO RELATED APPLICATIONS

This application is a U.S. National State entry of International Patent Application no. PCT/KR2020/006197, filed on May 11, 2020, which claims the benefit of priority of Korean Patent Application no. 10-2020-0056115, filed on May 11, 2020, and of Korean Patent Application no. 10-2019-0055063, filed on May 10, 2019.

TECHNICAL FIELD

The present disclosure relates to a DNA construct for diagnosing and treating cancer and a strain into which a recombinant vector comprising the DNA construct has been introduced.

BACKGROUND ART

To date, most cancers have been treated by each individual method corresponding to surgery, radiotherapy, chemotherapy, or a combination thereof. Surgical surgery that removes most of the cancerous tissue may be very effective at removing cancerous tissue located in a specific area, such as the breast, colon or skin, but is hardly used to treat cancerous tissue in some areas such as the spine. In addition, in the case of systemic chemotherapy that is commonly used for breast cancer, lung cancer and testicular cancer, side effects may occur which disrupt normal cell replication or metabolic processes, and resistance to therapeutic agents used in chemotherapy may occur in patients.

Meanwhile, when cancer occurs in an individual, blood vessel formation and cell growth proceed at a very fast rate in the body, and hence an oxygen-deficient environment may be created in the cancer tissue due to incomplete blood vessel formation, and the cancer tissue may be very suitable for growth of anaerobic bacteria such as *Salmonella* sp. strains or *Escherichia coli*. Accordingly, current cancer therapies that use bacteria capable of targeting cancer, such as *Salmonella* sp. strains and *Clostridium* sp. strains, rely upon the functions of specific bacteria that can target solid tumors and proliferate within the tumors. However, when an oncolytic protein or a reporter protein is introduced into the bacteria and the transformed bacteria are administered to an individual, it is possible to specifically identify cancer tissue or to treat cancer by minimizing side effects that are toxic to normal cells.

Diseases are caused in humans by toxins secreted from various bacterial pathogens that exist in nature. Among various bacterial pathogens that can cause diseases. *Salmonella enterica*, etc., which are closely related to our diet, are known as Enterobacteriaceae that inhabit the intestinal tracts of primates including humans, and secrete cytolysin known as an exotoxin. Cytolysin that is secreted in this way is a cytotoxic protein having a molecular weight of about 34 kDa, and is known to cause hemolysis (the destruction of red blood cells) in the intestines of primates including humans and to form pores in the membrane of normal cells to induce cell lysis, which leads to death due to severe vascular inflammation and the necrosis of local tissue. However, recent research results indicate that the cytolysin isolated and purified from *Salmonella enterica* acts specifically on cancer cells present in the intestinal tract, thereby inducing the death of the cancer cells. Thus, the cytolysin has attracted attention as a next-generation anticancer therapeutic agent. Therefore, bacteria transformed with a gene secreting the cytoxic substance cytolysin may have a very high potential for use as an anticancer therapeutic agent for targeting cancer tissue.

Although it is possible to diagnose or treat cancer using bacteria as described above, there have been few studies on expression vectors that allow proteins suitable for diagnosis and treatment to be expressed specifically in cancer tissues. After the bacteria are injected into a living body, clearance occurs in the reticuloendothelial systems such as the liver and spleen for the first 3 days, and then the bacteria increase rapidly in cancer tissue after a certain period of time. Thus, in terms of safety, it is required to allow the expression of a therapeutic protein after a certain period of time. Accordingly, the use of an inducible promoter for the expression of a therapeutic protein is recommended, but the clinical application of inducible promoters, such as a $P_{BAD}$ promoter currently used in the experimental stage, is greatly limited because L-arabinose, which is not permitted for human use, must be used as an inducer. A $P_{tet}$ promoter, which uses doxycycline, an antibiotic approved for human use, has advantages in that it is relatively easy to use clinically and allows bidirectional transcription of two genes using a TetA promoter and a TetR promoter. However, the difference in protein expression level between the TetA promoter and the TetR promoter is 100:1 or more, and thus the expression levels of these promotes need to be balanced to increase the utilization of the $P_{tet}$ promoter. Accordingly, it is necessary to develop a new technology for bacteria having a clinically applicable expression system and transformed such that protein expression levels can be balanced.

DISCLOSURE

Technical Problem

An object of the present disclosure is to provide a DNA construct.

Another object of the present disclosure is to provide a recombinant vector comprising the DNA construct.

Still another object of the present disclosure is to provide: a strain into which the recombinant vector has been introduced, and a composition for diagnosing cancer containing the strain.

Yet another object of the present disclosure is to provide a pharmaceutical composition for preventing or treating cancer containing the strain as an active ingredient.

Still yet another object of the present disclosure is to provide a method for providing information for diagnosing cancer, the method comprising a step of treating with the strain.

However, the technical problems to be solved by the present disclosure are not limited to the above-mentioned problems, and other problems not mentioned herein will be clearly understood by those skilled in the art from the following description.

Technical Solution

An embodiment of the present disclosure provides a DNA construct.

The DNA construct of the present disclosure comprises: a gene encoding a regulatory protein; and a first promoter and a second promoter, which are induced by the regulatory protein.

Any one selected from the group consisting of a gene encoding an anticancer protein, a gene encoding a cytokine, a gene encoding a chemokine, a gene encoding an immune modulator, a cancer antigen-specific oligonucleotide, and a gene encoding a reporter protein may be operably linked downstream of the first promoter and the second promoter of the present disclosure.

Since the first promoter and second promoter of the present disclosure are simultaneously inducible by a single regulatory protein expressed by a separate promoter, the expression levels of proteins encoded by the genes, operably linked downstream the first promoter and the second promoter, in a host strain or cell, may be balanced with each other, unlike the case in which the gene encoding the regulatory protein gene is operably linked downstream of the second promoter. Accordingly, when the DNA construct according to the present invention is used, diagnosis and treatment can be performed simultaneously.

The term "DNA construct" as used in the present disclosure refers to a construct that enables expression of a desired protein or the like when introduced into a host strain or cell by transformation, and comprises not only a gene encoding the desired protein, but also nucleotide sequences corresponding to promoters, which are essential regulatory elements operably linked so that the gene can be expressed.

The term "promoter" as used in the present disclosure refers to a nucleotide sequence which is present upstream of an operably linked gene in a host strain or cell, and is the nucleotide sequence of a specific region of the DNA construct to which RNA polymerase may bind in order to initiate transcription.

Expression of the regulatory protein of the present disclosure may be regulated by a cis-acting element (cis-regulatory elements; CRE) or a trans-acting factor (trans-regulatory elements; TRE).

In the present disclosure, the term "regulation" to "regulation of expression" may mean that transcription and translation of a specific gene are activated or inhibited.

The cis-acting factor of the present disclosure is a region of non-coding DNA that regulates the transcription of a neighboring gene, is an essential component of the gene regulatory network, and controls gene expression. The cis-acting factor may be at least one selected from the group consisting of a ribosome binding site (RBS), a 5'-untransrated region (5'-UTR), a transcription factor binding site and terminators, but is not limited thereto.

In the present disclosure, the ribosome binding site (RBS) is also referred to as the Shine-Dalgarno sequence (SD sequence). After the genetic information contained in DNA is transcribed into messenger RNA (mRNA), a ribosome must bind to this mRNA in order for translation to occur. At this time, the ribosome binding site means a short sequence that is present on the mRNA so that the ribosome can bind effectively to the mRNA.

In the present disclosure, the 5'-untranslated region (5'-UTR) refers to untranslated regions flanking both sides of a 5' coding region which is translated into amino acids of mRNA. It is considered a junk in the evolutionary process, but is known to play a major role in regulating gene expression.

In the present disclosure, the transcription factor binding site is a DNA region that serves to turn on or off a specific gene nearby. The transcription factor binding site may be at least one selected from the group consisting of a promoter, an enhancer, and a silencer of the gene encoding the regulatory protein, but is not limited thereto.

The promoter of the gene encoding the regulatory protein of the present disclosure may include any promoter whose activity can be induced in the environmental conditions and developmental conditions of most host strains or cells. Preferably, the promoter may be a weak promoter.

The "weak promoter" of the present disclosure is a promoter that induces a transcript, transcribed from the gene operably linked downstream thereof, to be expressed at a level of $1 \times 10^{-2}$ or less, preferably $1 \times 10^{-3}$ or less, and may include any promoter that allows the transcript to be expressed at a level of $1 \times 10^{-3}$ or less as described above. For example, the weak promoter may be at least one selected from the group consisting of an E. coli σ70 promoter, an E. coli σS promoter, an E. coli σ32 promoter, a B. subtilis σA promoter, a B. subtilis σB promoter, the Salmonella-derived promoter K112706 or K112707, a bacteriophage T7 promoter, a bacteriophage SP6 promoter, a yeast-derived promoter, the eukanrotic promoter 1712004 or K076017, an OXB1 promoter, and a plant-derived promoter, but is not limited thereto.

The E. coli σ70 promoter of the present disclosure may be at least one selected from the group consisting of I14018, I14033, I14034, I732021, I742126, J01006, J23103, J23109, J23112, J23113, J23117, J23119, J23150, J23151, J44002, J48104, J56015, J64951, K088007, K119000. K119001, K1330002, K137029, K137030, K137031, K137032, K137085, K137086, K137087, K137088, K137089, K137090, K137091, K1585100, K1585101, K1585102, K1585103, K1585104, K1585105, K1585106, K1585110, K1585113, K1585115, K1585116, K1585117, K1585118, K1585119, K2486171. K256002, K256018, K256020, K256033, K292000, K823007, K823010, K823013, M13101, M13102, M13103, M13104, M13105, M13106, M13108, M13110, M31519, R1074, R1075 and S03331, but is not limited thereto.

The E. coli σS promoter of the present disclosure may be J45992 or J45993, but is not limited thereto.

The E. coli σ32 promoter of the present disclosure may be J45504, K1895002 or K1895003, but is not limited thereto.

The B. subtilis σA promoter of the present disclosure may be at least one selected from the group consisting of K143012. K143013. K823000, K823002 and K823003, but is not limited thereto.

The B. subtilis σB promoter of the present disclosure may be K143010, K143011 or K143013, but is not limited thereto.

The bacteriophage T7 promoter of the present disclosure may be at least one selected from the group consisting of I719005, J34814, J64997, K113010, K113011, K113012, K1614000, R0085, R0180, R0181, R0182, R0183, Z0251, Z0252 and Z0253, but is not limited thereto.

The bacteriophage SP6 promoter of the present disclosure may be J64998, but is not limited thereto.

The yeast-derived promoter of the present disclosure may be at least one selected from the group consisting of 1766557, J63005, K105027, K105028, K105029, K105030, K105031, K122000, K124000, K124002, K319005, M31201, K2365040, K2365036, K2365041. K2365042, K2365032, K2365051, K2365514, K2365515 and K2365516, but is not limited thereto.

In the present disclosure, the weak promoter may be the OXB1 promoter represented by SEQ ID NO: 16, but is not limited thereto.

The plant-derived promoter of the present disclosure may be at least one selected from the group consisting of PLPR0203, PLPR0210, PLPR0177, PLPR0193, PLPR0507, PLPR0422, PLPR0228. PLPR0226, PLPR0223, PLPR0040, PLPR0465, PLPR0232, PLPR0205, PLPR0247, PLPR0328, PLPR0525, AtREG383, AtREG415, AtREG416, OsREG438, OsREG443, OsREG501, PpREG186, PpREG194 and PpREG197, but is not limited thereto.

For the purposes of the present disclosure, when the gene encoding the regulatory protein is operably linked downstream of the weak promoter, it is possible to control transcription such that transcription of the gene present downstream of the first and second promoters may occur specifically even when a substance that inhibits the regulatory protein is administered, unlike the case where the gene is operably linked downstream of the first promoter or the second promoter.

The promoter of the gene encoding the regulatory protein of the present disclosure may have the nucleotide sequence of SEQ ID NO: 8 corresponding to the −35 site from the gene encoding the regulatory protein, and the nucleotide sequence of SEQ ID NO: 9 corresponding to the −10 site, but is not limited thereto.

The enhancer of the present disclosure is a sequence found in both prokaryotes and eukaryotes, and generally has a 50 to 1,500 bp region, is located upstream or downstream from the starting point of the nearby gene, and induces binding of the transcription factor.

The silencer of the present disclosure has the same mechanism as the enhancer and antagonizes the enhancer effect. The transcription factor that binds to the silencer is a repressor. The enhancer and the silencer may be present in regions adjacent to each other, or may be present in the same region in which transcription factors thereof are different.

The terminators of the present disclosure are also referred to as transcription terminators, and mediate the termination of transcription of genes or operons in the genome. Prokaryotes include Rho-dependent terminators and Rho-independent terminators.

The trans-acting factor of the present disclosure is also referred to as a trans-activator or a trans-acting transcription factor, and is a factor that trans-activates the transcription of a gene. The trans-acting factor may be at least one selected from the group consisting of the transcription factor, an aptamer, sRNA, and antisense RNA (asRNA), but is not limited thereto.

In the present disclosure, the transcription factor is a protein that helps to turn on or off a specific gene by binding to the transcription factor binding site.

In the present disclosure, the aptamer is a part of a riboswitch, and collectively refers to oligonucleotide or peptide substances capable of binding to a specific target molecule. The aptamer is a peptide aptamer or a nucleic acid aptamer. The riboswitch is a kind of mRNA that regulates the expression of genes, and examples thereof include, but are not limited to, a glmS riboswitch, an FMN riboswitch, a Cobalamin riboswitch, and the like.

In the present disclosure, the sRNA or the antisense RNA (asRNA) refers to a single-stranded RNA capable of complementarily binding to a specific RNA. The antisense RNA binds complementarily to sense RNA, which is a messenger RNA (mRNA) expressing a specific protein, thereby regulating the expression of the protein.

The first promoter and the second promoter of the present disclosure may be inducible promoters that are induced by the regulatory protein.

The term "inducible promoter" as used in the present disclosure is a promoter that specifically transcribes the gene linked downstream thereof so that the gene can be expressed only under specific chemical or physical conditions. For example, the inducible promoter may be the LacZ gene promoter which is expressed in the presence of galactose such as isopropyl-β-D-1-thiogalactopyranoside (IPTG), the arabinose operon araBAD promoter which is expressed only in the presence of L-arabinose, or the tet promoter whose expression is regulated by tetracycline. Preferably, the first promoter and the second promoter may be the tet promoters. More preferably, the first promoter may be a tetA promoter, and the second promoter may be a tetR promoter, but the present disclosure is not limited thereto.

The gene encoding the regulatory protein of the present disclosure may be a protein that binds to the first promoter and the second promoter so that RNA polymerase cannot bind thereto. For the purposes of the present disclosure, when the first promoter and the second promoter are the tet promoters, the gene may be the TetR protein capable of inhibiting the activity of each tet promoter by binding to the regulatory region of each tet promoter, but is not limited thereto.

The term "operably linked" as used in the present disclosure means that one nucleic acid fragment of interest is functionally linked to another nucleic acid fragment so that the function or expression thereof is affected by the other nucleic acid fragment.

The term "reporter protein" as used in the present disclosure refers to a protein that functions so that cancer can be visually diagnosed. For example, the reporter protein may be, but is not limited to, at least one selected from the group consisting of a fluorescent protein, luciferase, and a protein that is used in nuclear medicine or MRI imaging.

The "fluorescent protein" in the present disclosure is a protein that fluoresces by itself so that cancer can be visually diagnosed. For example, the fluorescent protein may be at least one selected from the group consisting of green fluorescent protein (GFP), modified green fluorescent protein (MGFP), enhanced green fluorescent protein (EGFP), red fluorescent protein (RFP), enhanced red fluorescent protein (ERFP), blue fluorescent protein (BFP), enhanced blue fluorescent protein (EBFP), yellow fluorescent protein (YFP), and enhanced yellow fluorescent protein (EYFP), but is not limited thereto.

In the present disclosure, the protein that is used in nuclear medicine or MRI imaging may be, for example, at least one selected from the group consisting of herpes simplex virus thymidine kinase, dopamine receptor, somatostatin receptor, sodium-iodide transporter, iron receptor, transferrin receptor, ferritin and iron transporter (magA), but is not limited thereto.

The term "cytokine" as used in the present disclosure refers to proteins secreted by immune cells, and the cytokine of the present disclosure may include any cytokine that may be used in cancer immunotherapy capable of inducing the death of disease-related cells, for example, cancer cells, by regulating host immune response. Preferably, examples of the cytokine include, but are not limited to, IFN-α2, IL-2, IL-15, IL-21 and IL-12.

The term "chemokine" as used in the present disclosure refers to one functioning to control the migration of cells between tissues and the positioning and interactions of cells within tissues. The chemokine may include any chemokine that may mediate the host response to diseases, for example, cancer, by directing the trafficking of leukocytes into the tumor microenvironment. Preferably, examples of the chemokine include, but are not limited to, CXCR3, CCR5, etc.

The term "immune modulator" as used in the present disclosure refers to a modulator which enables various treatments by utilizing the intrinsic immune system of an individual, and may any modulator that can induce the death of disease-related cells, for example, cancer cells, by activating immune cells.

The "anticancer protein" of the present disclosure refers to a peptide having a function capable of directly or indirectly inducing the death of cancer cells. The anticancer protein may be, for example, at least one selected from the group consisting of a toxin protein, an antibody specific for a cancer antigen or a fragment of the antibody, a tumor suppressor protein, an angiogenesis inhibitor, a cancer antigen, a prodrug-converting enzyme, and a pro-apoptotic protein, but is not limited thereto.

The term "toxin protein" as used in the present disclosure refers to a protein having a function capable of directly or indirectly inducing the death of cancer cells. For example, the toxin protein may be at least one selected from the group consisting of ricin, saporin, gelonin, momordin, debouganin, diphtheria toxin, *Pseudomonas* toxin, hemolysin (HlyA), FAS ligand (FASL), tumor necrosis factor-α (TNF-α), TNF-related apoptosis-inducing ligand (TRAIL) and cytolysin A (ClyA). More preferably, the toxin protein may be cytolysin A consisting of the amino acid sequence represented by SEQ ID NO: 1, but is not limited thereto.

The term "tumor suppressor protein" as used in the present disclosure refers to a gene which maintains its function in normal cells, but causes normal cells to indiscriminately divide and grow into cancer cells when the function thereof is lost. Examples of the tumor suppressor protein include, but are not limited to, retinoblastoma (RB) protein, p53 protein, adenomatous polyposis *coli* (APC) protein, phosphatase and tensin homologue (PTEN) protein, cyclin dependent kinase inhibitor 2A (CDKN2A) protein, and the like.

In the present disclosure, the antibody specific for cancer antigen and the fragment of the antibody is an antibody capable of specifically binding to an antigen which is a protein having a high expression level specifically on the surface or cytoplasm of a cancer cell. For example, the antibody or the fragment thereof may be an antibody specific for HER2 having a high expression level specifically in breast cancer or gastric cancer cells, but is not limited thereto.

The term "antibody" as used in the present disclosure refers to a protein molecule capable of binding specifically to an antigenic site of a protein or peptide molecule. The type of the antibody is not particularly limited, and examples thereof include polyclonal antibodies, monoclonal antibodies, or antibody fragments having an antigen-binding property, and include all types of immunoglobulin antibodies. In addition, examples of the antibody include specific antibodies such as humanized antibodies. Examples of the antibody include not only a whole antibody having two full-length light chains and two full-length heavy chains, but also a functional fragment of an antibody molecule. The "functional fragment of an antibody molecule" refers to a fragment having at least an antigen-binding function, and examples thereof include, but are not limited, Fab, F(ab'), F(ab')2, Fv, etc.

The antibody of the present disclosure may be produced by a conventional method after cloning the gene encoding the cancer antigen of the present disclosure into an expression vector according to a conventional method to obtain a protein encoded by the gene.

The term "angiogenesis inhibitor" as used in the present disclosure refers to a protein or compound having a function capable of directly or indirectly inducing the death of cancer cells by inhibiting the formation of new blood vessels around cancer cells. Preferably, examples of the angiogenesis inhibitor include, but are not limited to, angiostatin, endostatin, thrombospondin, and protease inhibitory proteins.

The term "cancer antigen" as used in the present disclosure refers to a protein antigen which is expressed in cancer cells but is rarely expressed in normal cells, thereby inducing an anti-tumor immune response, thereby inducing the direct or indirect death of cancer cells. Preferably, the cancer antigen of the present disclosure may be α-fetoprotein (AFP), vascular endothelial growth factor receptor 2 (VEGFR2), Survivin, Legumain, prostate cancer-specific antigen (PCSA), or the like, but is not limited thereto.

The term "prodrug converting enzyme" as used in the present disclosure refers to a protein having a function of converting an inactive drug into an active drug through a metabolism caused by an enzymatic reaction. When this prodrug converting enzyme is used, the inactive drug can be metabolized and converted into an active drug capable of directly or indirectly inducing the death of cancer cells. Thus, the prodrug converting enzyme may be very useful for the prevention or treatment of cancer. Preferred examples of the prodrug converting enzyme of the present disclosure include, but are not limited to, thymidine kinase, cytosine deaminase, nitroreductase, purine nucleoside phosphorylase, carboxypeptidase G2, chromate reductase YieF, herpes simplex virus type I thymidine kinase/ganciclovir (HSV1-TK/GCV), β-glucuronidase, and the like.

The term "pro-apoptotic protein" as used in the present disclosure refers to a protein that induces the direct or indirect death of cancer cells by making these cells deficient in factors (proteins, nutrients, oligonucleotides, etc.) essential for growth or maintenance of the cancer cells. Preferred examples of the pro-apoptotic protein of the present disclosure include, but are not limited to, L-ASNase, RNA-binding motif protein 5 (RBM5), and the like.

The cancer antigen-specific oligonucleotide of the present disclosure refers to a nucleotide capable of inhibiting the expression or function of a cancer antigen by complementary binding to a gene or mRNA of the cancer antigen, and may be any one selected from the group consisting of an antisense oligonucleotide, an aptamer, siRNA and shRNA, but is not limited thereto.

The term "antisense oligonucleotide" as used in the present disclosure refers to DNA, RNA, or a derivative thereof, which comprises a nucleic acid sequence complementary to a specific mRNA sequence and is capable of inhibiting the translation of mRNA into protein by binding to the complementary sequences in mRNA. The antisense oligonucleotide may be synthesized in vitro by a conventional method using, for example, RNA polymerase I, and then administered in vivo, or it may be synthesized in vivo by a method using a vector having a multiple cloning site (MCS) in opposite orientation.

The term "aptamer" as used in the present disclosure refers to a small single-stranded oligonucleotide capable of specifically recognizing a target substance with high affinity. For the purposes of the present disclosure, the target substance may be a gene or mRNA of a cancer antigen.

The term "siRNA" as used in the present disclosure refers to a short double-stranded RNA capable of inducing an RNA interference (RNAi) phenomenon by cleavage of a specific mRNA. The siRNA is composed of a sense RNA strand having a sequence homologous to the mRNA of a target gene and an antisense RNA strand having a sequence complementary thereto. For the purposes of the present disclosure, the siRNA may bind specifically to an mRNA transcribed from a gene encoding a cancer antigen, thereby effectively inhibiting the expression of this gene.

The term "shRNA" as used in the present disclosure refers to a short hairpin RNA. The shRNA has advantages in that the cell transfection rate thereof is higher than that of siRNA and that RNA interference can be maintained for a long period of time.

RNA interference can be induced by, but not limited to, the process of transforming adenovirus, lentivirus and plasmid expression vector systems from the promoter of RNA polymerase III into cells, followed by expression. For the purposes of the present disclosure, the shRNA may specifically bind to mRNA transcribed from a gene encoding a cancer antigen, thereby effectively inhibiting the expression of this gene.

Another embodiment of the present disclosure provides a recombinant vector comprising the DNA construct of the present disclosure.

As the recombinant vector of the present disclosure comprises the DNA construct of the present disclosure, the regulatory protein is expressed by a separate promoter, and thus the genes operably linked downstream of the first promoter and the second promoter may be expressed in a balanced manner, specifically only when a substance that inhibits the regulatory protein is externally administered.

In the recombinant vector of the present disclosure, details regarding the DNA construct, anticancer protein, cytokine, chemokine, immune modulator, cancer antigen-specific oligonucleotide, reporter protein and promoter, etc. are the same as described above with respect to the DNA construct, and thus the repeated description thereof will be omitted in order to avoid excessive complexity of the present specification.

The recombinant vector of the present disclosure is a means for expressing a protein by introduction into a cell, and may be a known recombinant vector such as a plasmid vector, a cosmid vector or a bacteriophage vector. The recombinant vector may be readily produced by those skilled in the art according to any known method using DNA recombination technology.

In the present disclosure, specific examples of the recombinant vector may be selected from the group consisting of a pCDNA vector which is commercially widely used, F, R1, Col, pBR322, ToL, Ti vector, cosmid, phages such as lambda, lambdoid, M13, Mu, p1 P22, Qμ, T-even, T2, T3, or T7, and plant viruses, but are not limited thereto. For the purposes of the present disclosure, a suitable recombinant vector may be selected according to the nature of the host cell.

Another embodiment of the present disclosure provides a host cell or strain into which a recombinant vector comprising the DNA construct of the present disclosure has been introduced.

The host cell of the present disclosure may include cells of mammalian, plant, insect, fungal or cellular origin. For example, the host cell may be, but is not limited to, at least one selected from the group consisting of bacterial cells such as Escherichia coli, Streptomyces or Salmonella sp. strains; fungal cells such as yeast cells or Pichia pastoris; insect cells such as Drosophila or Spodoptera Sf9 cells; animal cells such as Chinese hamster ovary (CHO) cells, SP2/0 (mouse myeloma), human lymphoblastoid, COS, NSO (mouse myeloma), 293T cells, bow melanoma cells, HT-1080 cells, baby hamster kidney (BHK) cells, human embryonic kidney (HEK) cells, or PERC.6 cells (human retinal cells; and plant cells. For the purposes of the present disclosure, the strain may be at least one selected from the group consisting of anaerobic strains, for example, Salmonella sp. strains, Clostridium sp. strains, Bifidobacterium sp. strains, and E. coli strains. Preferably, the strain may be at least one selected from the group consisting of Salmonella typhimurium, Salmonella choleraesuis and Salmonella enteritidis. More preferably, the strain may be Salmonella typhimurium, but is not limited thereto.

The strain of the present disclosure may be an attenuated strain.

The term "attenuated" as used in the present disclosure means modifying a gene or the like so as to reduce toxicity and other side effects, which may occur when a microorganism is administered to a patient. For the purposes of the present disclosure, when the strain is a Salmonella sp. strain, at least one gene selected from the group consisting of aroA, aroC, aroD, aroE, Rpur, htrA, ompR, ompF, ompC, galE, cva, crp, cyp, phoP, phoQ, rfaY, dks, hupA, sipC, clpB, clpP, clpX, pah, nadA, pncB, pmi, rpsL, hemA, rfc, poxA, gaLU, cdt, pur, ssa, guaA, guaB, fliD, flgK, flgL, reLA and spoA may be modified for attenuation, but the gene is not limited thereto.

The method for modifying the gene of the present disclosure may be performed by a method of deleting or disrupting various genes as known in the art. For example, the deletion or disruption method may be performed by a method such as homologous recombination, chemical mutagenesis, irradiation mutagenesis or transposon mutagenesis.

In the present disclosure, the strain targets the inside of cancer tissue, which is an oxygen-deficient environment which is very suitable for the growth of an anaerobic strain and shows incomplete blood vessel formation, and thus when a recombinant vector comprising a reporter protein that may be imaged in real time and an anticancer protein is introduced into this strain so that the expression levels of the reporter protein and the anticancer protein can be balanced, it is possible to very effectively diagnose and treat cancer.

In the strain of the present disclosure, details regarding the DNA construct, anticancer protein, cytokine, chemokine, immune modulator, cancer antigen-specific oligonucleotide, reporter protein, promoter and recombinant vector, etc., are the same as described above with respect to the DNA construct and the recombinant vector, and thus the repeated description thereof will be omitted in order to avoid excessive complexity of the present specification.

The recombinant vector of the present disclosure may be introduced into a host cell or a strain by transformation (or transfection), and the transformation method that is used in the present disclosure may be any transformation method and may be easily performed according to a conventional method known in the art. Specifically, the recombinant vector may be introduced into the strain by a method for transformation of bacteria such as the Salmonella sp. strain, which may be commonly used, CaCl$_2$ precipitation, Hanahan method that uses DMSO (dimethyl sulfoxide) as a reducing material in addition to the CaCl$_2$ method to increase efficiency, electroporation, calcium phosphate precipitation, protoplast fusion, an agitation method using silicon carbide fibers, Agrobacterium mediated transformation, transformation using PEG, a method using dextran sulfate, a method using lipofectamine, or desiccation/inhibition-mediated transformation, but the transformation method is not limited thereto.

Another embodiment of the present disclosure provides a pharmaceutical composition for preventing or treating cancer.

The pharmaceutical composition of the present disclosure contains the strain of the present disclosure as an active ingredient.

As the strain of the present disclosure is transformed with the DNA construct of the present disclosure, it may target cancer in an individual, and then the reporter protein that may be imaged in real time and the anticancer protein in this strain may be expressed in a balanced manner when a substance that inhibits the regulatory protein is administered. Thus, the strain may very effectively prevent or treat cancer, and at the same time, may diagnose cancer in real time.

The term "cancer" as used in the present disclosure refers to a disease characterized by rapid and uncontrolled growth of mutant cells. The cancer may be at least one selected from the group consisting of melanoma, fallopian tube cancer, brain cancer, small intestine cancer, esophageal cancer, lymph adenocarcinoma, gallbladder cancer, blood cancer, thyroid cancer, endocrine adenocarcinoma, oral cancer, liver cancer, biliary tract cancer, colorectal cancer, rectal cancer, cervical cancer, ovarian cancer, kidney cancer, stomach cancer, duodenal cancer, prostate cancer, breast cancer, brain tumor, lung cancer, undifferentiated thyroid cancer, uterine cancer, colon cancer, bladder cancer, ureter cancer, pancreatic cancer, bone/soft tissue sarcoma, skin cancer, non-Hodgkin's lymphoma, Hodgkin's lymphoma, multiple myeloma, leukemia, myelodysplastic syndrome, acute lymphoblastic leukemia, acute myeloid leukemia, chronic lymphocytic leukemia, chronic myelogenous leukemia, and solitary myeloma. Preferably, the cancer may be at least one selected from the group consisting of liver cancer, biliary tract cancer, colorectal cancer, rectal cancer, cervical cancer, ovarian cancer, kidney cancer, stomach cancer, duodenal cancer, prostate cancer, breast cancer, brain tumor, lung cancer, undifferentiated thyroid cancer, uterine cancer, colon cancer, bladder cancer, ureter cancer, pancreatic cancer, bone/soft tissue sarcoma, and skin cancer. More preferably, the cancer may be colon cancer, but is not limited thereto.

The term "preventing" as used in the present disclosure may include, without limitation, any action that blocks symptoms caused by cancer or suppresses or delays the symptoms, by using the active ingredient of the present disclosure.

The term "treating" as used in the present disclosure refers to any action that beneficially changes symptoms caused by cancer or benefits an individual, by using the active ingredient of the present disclosure, and refers to an approach for obtaining beneficial or desired results, including clinical results. Beneficial or desired clinical results may include, but are not limited to, alleviation or amelioration of one or more symptoms or conditions; diminishment of extent of disease; stabilization of the state of disease; prevention of development of disease; prevention of spread of disease; delay or slowing of disease progression, delay or slowing of disease onset, amelioration or palliation of the disease state; and remission (whether partial or total), whether detectable or undetectable. "Treating" can also mean prolonging survival of a patient beyond that expected in the absence of treatment. In addition, "treating" can also mean inhibiting the progression of disease or slowing the progression of disease temporarily, although more preferably, it involves halting the progression of the disease permanently. As will be understood by a skilled person, results may not be beneficial or desirable if, while improving a specific disease state, the treatment results in adverse effects on the patient treated that outweigh any benefits effected by the treatment.

In the pharmaceutical composition of the present disclosure, details regarding the DNA construct, anticancer protein, cytokine, chemokine, immune modulator, cancer antigen-specific oligonucleotide, reporter protein, promoter recombinant vector, strain and transformation, etc. are the same as described above with respect to the DNA construct, the recombinant vector and the strain, and thus the repeated description thereof will be omitted in order to avoid excessive complexity of the present specification.

The pharmaceutical composition of the present disclosure may be in the form of capsules, tablets, granules, injections, ointments, powders or beverages, and the pharmaceutical composition may be for administration to humans.

For use, the pharmaceutical composition of the present disclosure may be formulated in the form of, but not limited to, oral dosage forms such as powders, granules, capsules, tablets, aqueous suspensions, etc., external preparations, suppositories, and sterile injection solutions, according to the respective conventional methods. The pharmaceutical composition of the present disclosure may contain pharmaceutically acceptable carriers. Pharmaceutically acceptable carriers that may be used for oral administration include binders, lubricants, disintegrants, excipients, solubilizers, dispersants, stabilizers, suspending agents, pigments, flavorings, and the like, and pharmaceutically acceptable carriers that may be used for injection include buffers, preservatives, analgesics, solubilizers, isotonic agents, stabilizers, and the like. Pharmaceutically acceptable carriers that may be used for topical administration include bases, excipients, lubricants, preservatives, and the like. The dosage forms of the pharmaceutical composition of the present disclosure may be prepared in various ways by mixing with pharmaceutically acceptable carriers as described above. For example, for oral administration, the pharmaceutical composition may be prepared in the form of tablets, troches, capsules, elixir, suspensions, syrups, wafers, and for injection, the pharmaceutical composition may be presented in unit dose ampoules or multi-dose containers. In addition, the pharmaceutical composition may be formulated as solutions, suspensions, tablets, capsules, sustained-release preparations, or the like.

Meanwhile, examples of carriers, excipients and diluents suitable for formulation include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil. In addition, the pharmaceutical composition may further contain a filler, an anticoagulant, a lubricant, a wetting agent, a fragrance, an emulsifier, a preservative, or the like.

The routes of administration of the pharmaceutical composition according to the present disclosure include, but are not limited to, oral, intravenous, intramuscular, intra-arterial, intramedullary, intradural, intracardiac, transdermal, subcutaneous, intraperitoneal, intranasal, gastrointestinal, topical, sublingual and intrarectal routes. Oral or parenteral administration is preferred.

In the present disclosure, "parenteral" includes subcutaneous, transdermal, intravenous, intramuscular, intra-articular, intra-synovial, intrasternal, intradural, intra-lesional and intra-cranial injection or infusion techniques. The pharmaceutical composition of the present disclosure may also be formulated as suppositories for intrarectal administration.

The pharmaceutical composition of the present disclosure may vary depending on various factors, including the activity of a specific compound used, the patient's age, body weight, general health, sex, diet, the time of administration, the route of administration, excretion rate, the drug content, and the severity of a specific disease to be prevented or treated. The dose of the pharmaceutical composition may be suitably selected by a person skilled in the art depending on the patient's condition, body weight, the severity of the disease, the form of drug, and the route and period of administration, and may be 0.0001 to 50 mg/kg/day or 0.001 to 50 mg/kg/day. The pharmaceutical composition may be administered once or several times a day. The dose is not intended to limit the scope of the present disclosure in any way. The pharmaceutical composition according to the present disclosure may be formulated as pills, sugar-coated tablets, capsules, liquids, gels, syrups, slurries, or suspensions.

Another embodiment of the present disclosure provides a composition for diagnosing cancer.

The diagnostic composition of the present disclosure contains the strain of the present disclosure as an active ingredient.

As the strain of the present disclosure is transformed with the DNA construct of the present disclosure, it may target cancer cells in an individual, and then the reporter protein that may be imaged in real time and the anticancer protein in this strain may be simultaneously expressed in a balanced manner when a substance that inhibits the regulatory protein is administered. Thus, the strain may very effectively prevent or treat cancer, and at the same time, may diagnose cancer in real time.

The term "diagnosing" as used in the present disclosure refers to any action that detects cancer tissue in vivo, including monitoring the presence of cancer in real time by the reporter protein expressed from the DNA construct introduced into the strain, when the strain of the present disclosure is located by targeting cancer.

In the diagnostic composition of the present disclosure, details regarding on the DNA construct, anticancer protein, reporter protein, constitutive promoter, inducible promoter, recombinant vector, *Salmonella* sp. strain, transformation, cancer, etc., are the same as described above with respect to the DNA construct, the recombinant vector, the strain and the pharmaceutical compositions, and thus the repeated description thereof will be omitted in order to avoid excessive complexity of the present specification.

Another embodiment of the present disclosure provides a method for providing information for diagnosing cancer.

The method of the present disclosure comprises a step of treating a biological sample, isolated from a subject of interest, with the strain into which the recombinant vector according to the present disclosure has been introduced.

The method for providing information for diagnosing cancer according to the present disclosure may further comprises a step of diagnosing cancer when the reporter protein is expressed from the strain.

The term "biological sample" as used in the present disclosure refers to any material, tissue or cell obtained or derived from the subject. Examples of the biological sample include, but are not limited to, tissues, cells, or cell extracts.

In the method for providing information for diagnosing cancer according to the present disclosure, details regarding the DNA construct, anticancer protein, cytokine, chemokine, immune modulator, cancer antigen-specific oligonucleotide, reporter protein, promoter, recombinant vector, strain, transformation, cancer, diagnosis, etc. are the same as described above with respect to in the DNA construct, the recombinant vector, the strain, the pharmaceutical composition, and the diagnostic composition, and thus the repeated description thereof will be omitted in order to avoid excessive complexity of the present specification.

Another embodiment of the present disclosure is directed to a method for preventing or treating cancer, the method comprising a step of administering to a subject a pharmaceutically effective amount of the strain according to the present disclosure.

The term "subject" as used in the present disclosure refers to a subject in need of prevention or treatment of cancer. Examples of the subject include, but are not limited to, primates, for example, humans, and all mammals such as cattle, horses, sheep, pigs, goats, camels, antelopes, dogs, and cats.

Advantageous Effects

The DNA construct according to the present disclosure enables simultaneous diagnosis and treatment of cancer, because it allows the expression levels of genes, operably linked downstream of the first promoter and the second promoter, in a host strain or cell, to be balanced with each other.

In addition, since the DNA construct of the present disclosure cannot allow the anticancer protein and reporter protein to be expressed at all in the absence of doxycycline, it enables an anticancer protein to be expressed at an appropriate dose for cancer treatment by controlling whether or not treatment with doxycycline is performed, and at the same time, enables the size of the cancer to be monitored in real time depending on the expression level of the reporter protein.

BEST MODE

One embodiment of the present disclosure provides a DNA construct.

MODE FOR INVENTION

Hereinafter, the present disclosure will be described in more detail through examples. It will be obvious to those skilled in the art that these examples are only for explaining the present disclosure in more detail, and the scope of the present disclosure according to the subject matter of the present disclosure is not limited by these examples.

EXAMPLES

[Preparation Example 1] Construction of DNA Constructs Controllable by Doxycycline

[1-1] Construction of DNA Constructs Comprising OXB1 Promoter

Figure 1:
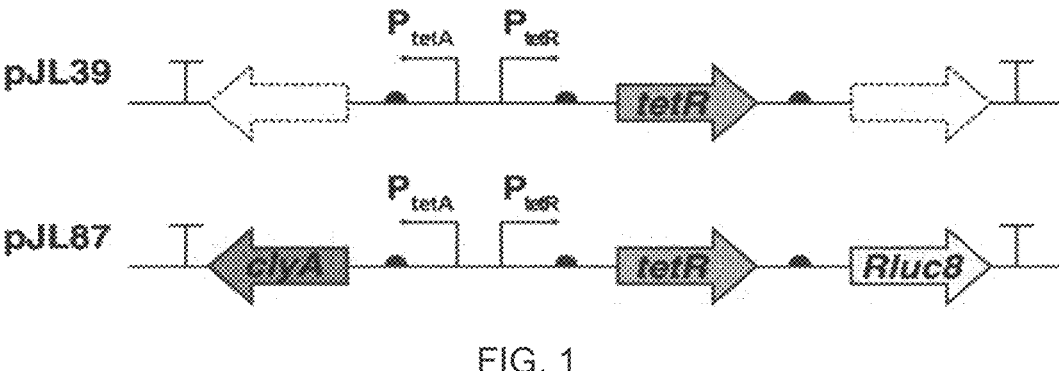
FIG. 1 is a schematic view of a DNA construct according to one embodiment of the present disclosure.

Using a pJL39 plasmid (*Mol Ther.*, 21(11), p. 1985-1995, (2013)) as a template strand (FIG. 1), a tetR gene was amplified using a forward primer (5'-CGGAATTCAC-CATGTCTAGATTAGATAAAAGTAAAGTGAT-TAACAG-3'; SEQ ID NO: 2), constructed to include the restriction enzyme EcoRI site, and a reverse primer (5'-GCTCTAGACAGCTGTTAAGACCCACTTTCACATT-TAAGTTGTTTTTCT-3; SEQ ID NO: 3) constructed to include the restriction enzyme PvuII-XbaI site. Thereafter, the amplification product was cleaved with the restriction enzymes EcoRI and XbaI and purified to obtain a tetR gene amplification product which was then introduced into a pBAD24 (Catalog No. ATCC® 87399™, ATCC, USA) plasmid, thereby constructing a pBAD-TetR plasmid.

Thereafter, through PvuII and HindIII fragments of the pJL39 plasmid, a divergent promoter region containing a multiple cloning site was introduced into the pBAD-TetR plasmid, thereby constructing a pTetR-BAD plasmid. Using NheI and PciI restriction enzymes, the araC and araBAD promoter were removed from the pTetR-BAD plasmid, thereby constructing a pTetII plasmid.

The constitutive promoter OXB1 (SEQ ID NO: 16), obtained by amplification using pSF-OXB1 (Oxford Genetics, England) as a template and a forward primer (5'-CTACTCCGTCAAGCCGTCAAGCTGTTGTGACCGCT TGCT-3'; SEQ ID NO. 4) and a reverse primer (5'-TGAAT-TCCTCCTGCTAGCTAGTTGGTAACGAATCA- GACGCCGGGTAATACCG GATAG-3'; SEQ ID NO: 5), was introduced into the pTetII plasmid by the Gibson assembly method, thereby constructing a pJH18 plasmid comprising the OXB1, tetA and tetR promoters.

Figure 2:
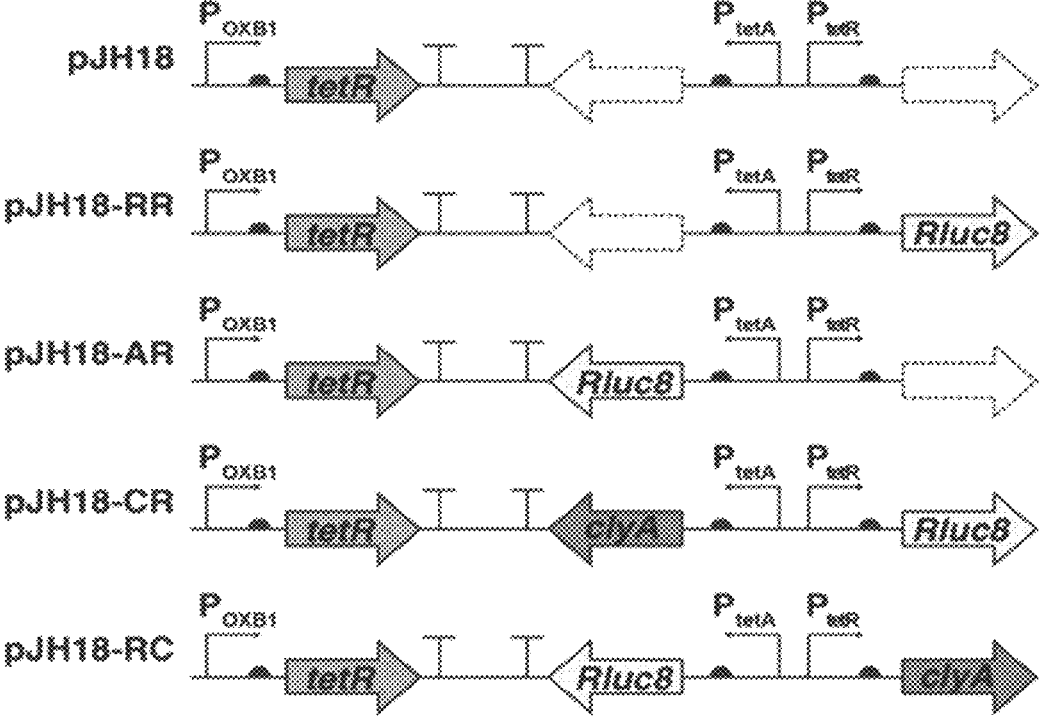
FIG. 2 is a schematic view of a DNA construct according to one embodiment of the present disclosure.

Using the pJH18 plasmid as a backbone, the genes encoding tetR. Rluc8 and cytolysin A (ClyA) were introduced downstream of the promoters in the combinations shown in Table 1 below, thereby constructing pJH18-RR, pJH18-AR and pJH18-CR plasmids (FIG. 2).

TABLE 1

| Plasmid | OXB1 | tetA | tetR |
|---|---|---|---|
| pJH18-RR | tetR | — | Rluc8 |
| pJH18-AR | tetR | Rluc8 | — |
| pjH18-CR | tetR | cly A | Rluc8 |

[1-2] Construction of DNA Constructs Comprising OXB11, 13 and 20 Promoters

In the same manner as in Preparation Example [1-1] above, each of the constitutive promoters OXB11, OXB13 and OBX20, obtained by amplification using pSF-OXB11, pSF-OXB13 or pSF-OXB20 as a template and a forward primer (5'-TGCTACTCCGTCAAGCCGT-CAAGCTGTTGTGACCGCTTG-3': SEQ ID NO: 6) and a reverse primer (5'-AGCTTGGTAACGAATCA-GACGCCGGGTAATACCGGATAG-3': SEQ ID NO: 7), was introduced into the pJH18 plasmid, constructed in Preparation Example [1-1] above, by the Gibson assembly method (pTetOXB11-AR, pTetOXB11-RR, pTetOXB13-AR, pTetOXB13-RR, pTetOXB20-AR, and pTetOXB20-RR). Here, the efficiency of protein expression by the plasmid is higher in the order of OXB11, OXB13 and OXB20, and OXB1 shows the weakest protein expression efficiency.

[1-3] Construction of DNA Construct Comprising Tac Promoter

The constitutive promoter Tac was introduced into the pJH18 plasmid constructed in Preparation Example [1-1] above. Specifically, the constitutive promoter Tac sequence was amplified using a Tac forward primer (5'-CCCTATGC-TACTCCGTCAAGCCGTCAATTGTTGACAATTAAT-CATCGGCTCGT ATAATGTCTGATTCGTTACCAAGCT-3': SEQ ID NO: 10) and a Tac reverse primer (5'-AGCTTGGTAACGAATCAGACATTATACGAGCC GATGATTAATTGTCAACAAT TGACGGCTTGACG-GAGTAGCATAGGG-3': SEQ ID NO: 11), and then the Tac promoter was introduced into the pJH18 plasmid by the Gibson assembly method, thereby constructing a pTetTac-RR plasmid.

[1-4] Construction of DNA Construct Comprising J23101 Promoter

Likewise, the constitutive promoter J23101 was introduced into the pJH18 plasmid constructed in Preparation Example 11-11 above. Specifically, the constitutive promoter J23101 sequence was amplified using a J23101 forward primer (5'-TGCTACTCCGTCAAGCCGTCTTTA-CAGCTAGCTCAGTCCTAGGTATAATGCTA GCCAATTGTCTGATTCGTTACC-3': SEQ ID NO: 12) and a J23101 reverse primer (5'-GGTAACGAATCA-GACAATTGGCTAGCATTATACCTAGGACT-GAGCTAGCTGT AAAGACGGCTTGACGGAGTAGCA-3': SEQ ID NO: 13), and then the J23101 promoter was introduced into the pJH18 plasmid by the Gibson assembly method, thereby constructing a pTetJ23101-RR plasmid.

[1-5] Construction of DNA Construct Comprising J23119 Promoter

Likewise, the constitutive promoter J23119 was introduced into the pJH18 plasmid constructed in Preparation Example [1-1] above. Specifically, the constitutive promoter J23119 sequence was amplified using a J23119 forward primer (5'-TGCTACTCCGTCAAGCCGTCT TGACAGCTAGCTCAGTCCTAGGTATAATGCT AGC-CAATTGTCTGATTCGTTACC-3': SEQ ID NO: 14) and a J23119 reverse primer (5'-GGTAACGAATCAGACAAT-TGGCTAGCATTATACCTAGGACTGAGCTAGCTGT CAAGACGGCTTGACGGAGTAGCA-3'; SEQ ID NO: 15), and then the J23119 promoter was introduced into the pJH18 plasmid by the Gibson assembly method, thereby constructing a pTetJ23119-RR plasmid.

[Preparation Example 2] Cancer Cell Lines and Culture Conditions

The CT26 colon cancer cell lines CRL-2638 and HB-8064 (ATCC, USA) and the murine colorectal adeno-carcinoma cell line MC38 (Massachusetts General Hospital and Harvard Medical School, USA and Chonnam National University, Korea) were used in the experiment.

Using high-glucose DMEM (Dulbecco's Modified Eagles Medium)(Catalog No. #LM 001-05, Welgene, Korea) containing 10% fetal bovine serum (FBS) and 1% penicillin-streptomycin, the cells were cultured in a 5% $CO_2$ incubator at 37° C.

[Preparation Example 3] Construction of *Salmonella* Strains Having Plasmids Introduced Therein As a *Salmonella* strain, SHJ2037 (relA::cat, spoT::kan), which is ppGpp-deficient *Salmonella typhimurium* (*S. typhimurium*), was used.

Each of the plasmids constructed in Preparation Example 1 above was transformed into the *Salmonella* strain by electroporation, and each of the transformed strains was cultured overnight in an LB containing 100 µg/ml ampicillin. Thereafter, each of the cultures was diluted at a ratio of 1:100 with a fresh LB medium containing ampicillin and further cultured. When the $OD_{600}$ value reached 0.5 to 0.7, doxycycline diluted with ethanol to a final concentration of 0, 10, 50, 100, 300 or 500 ng/ml was added to the cultures which were then cultured in a shaking incubator under conditions of 200 rpm and 37° C.

[Preparation Example 4] Preparation of Experimental Animal Models 5 to 6-week-old C57BL/6 and BALB/C mice (Orient Company, Korea) weighing 20 to 30 g were used. MC38 or CT26 of Preparation Example 2 was subcutaneously injected into the flank of each of the mice, thereby constructing tumor animal models.

For imaging of the tumor animal model and evaluation of the tumor volume, 2% isoflurane was used for anesthesia, and 200 mg/kg of ketamine and 10 mg/kg of xylasine were used during surgery.

The tumor volume (mm$^3$) was calculated using the equation "(length×height×width)/2", and when the tumor volume in the animal model reached 1,500 mm$^3$ or larger, the animal model was euthanized.

[Example 1] Prediction of tetR Promoter in pTetII Plasmid

Figure 3:
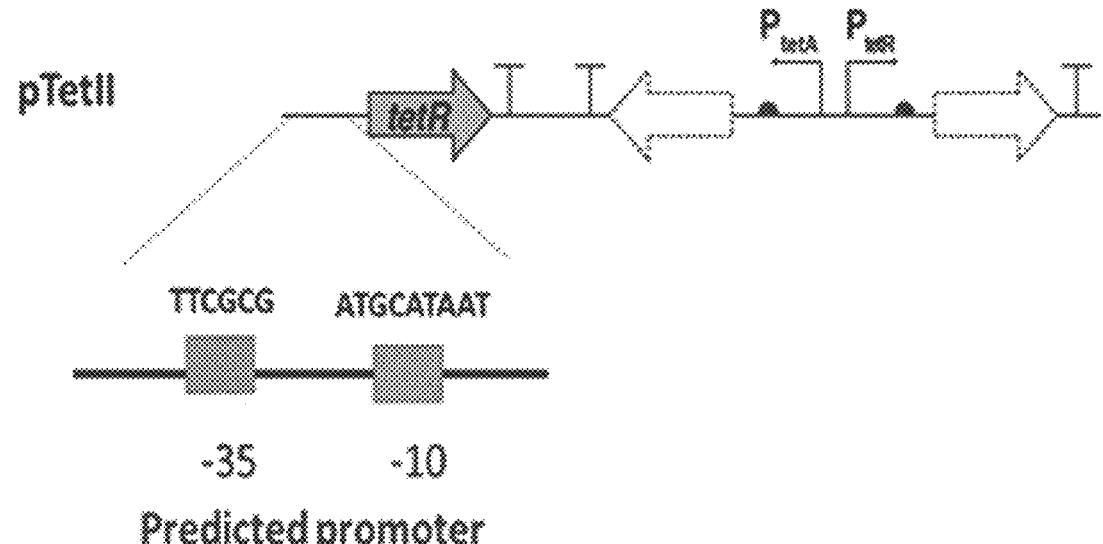
FIG. 3 is a schematic view showing the nucleotide sequences of the −35 site and −10 site of the predicted terR protein promoter in a DNA construct according to one embodiment of the present disclosure.

In the pTetII plasmid prepared as an intermediate product in Preparation Example [1-1], the sequence of the promoter capable of controlling the expression of tetR protein was predicted using BPROM (bacterial sigma 70 promoter prediction program), and the results is shown in FIG. 3.

As shown in FIG. 3, the nucleotide sequence of SEQ ID NO: 6 at the −35 site from the tetR protein in the pTetII plasmid was predicted, and the nucleotide sequence of SEQ ID NO: 7 at the −10 site from the tetR protein was predicted.

From the above results, it can be seen that, even when the pTetII plasmid according to the present disclosure does not comprise a separate promoter such as OXB1, tetR protein can be expressed naturally when SEQ ID NOs: 6 and 7 can be located at the −35 and −10 sites, respectively.

[Example 2] Comparison of Protein Expression Levels and Luciferase Activities in Strains Having PJH18-RR and PJH18-AR Plasmids Introduced Therein

[2-1] Comparison of Protein Expression Levels by Western Blot Analysis and Coomassie Blue Staining In order to examine the expression levels of the genes introduced downstream of the tetA and tetR promoters in each of the plasmids constructed in Preparation Example [1-1] are balanced with each other, the Rluc8 protein expressed in the strain of Preparation Example 3, into which each of the plasmids constructed in Preparation Example [1-1] has been introduced, was stained with Coomassie blue dye, or Western blot analysis was performed using an antibody specific for the protein.

Specifically, a culture of the strain of Preparation Example 3 was diluted with PBS to a concentration of $4×10^7$ CFU/ml and centrifuged at 13,000 rpm for 5 minutes, and the pellet fraction was collected. The pellet fraction was washed with PBS and mixed with an SDS sample buffer containing 0.2% β-mercaptoethanol (Catalog No. EBA-1052. ELPIS BIO-TECH) to obtain a strain lysate. Thereafter, the strain lysate was electrophoresed on 15% SDS-PAGE gel, and the gel was stained with Coomassie blue dye, or the protein on the gel was transferred to a nitrocellulose membrane and blocked with 5% skim milk at room temperature. Thereafter, the expression level of the Rluc8 protein was analyzed using Rluc8 antibody (Catalog No. AB3256, Millipore, USA), and the results are shown in FIG. 4.

Figure 4:
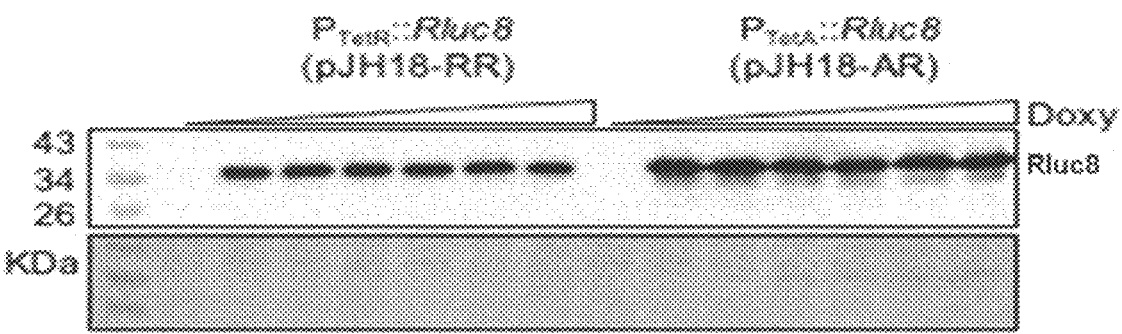
FIGS. 4 to 6 show the results of analyzing of the luciferase activity of a reporter protein according to one embodiment of the present disclosure.

As shown in FIG. 4, the level of the RLuc8 protein expressed from the tetA promoter was 2 to 6 times higher than the level of the protein expressed from the tetR promoter, and was very sensitive to the concentration of the saturated inducer even at the lowest concentration of doxycycline (10 ng/ml).

[2-2] Comparison of Functional Expression Level of Protein by Luciferase Activity Assay In order to measure the luciferase activity in the strain of Comparative Example 3, into which each of the plasmids constructed in Preparation Example [1-1] has been introduced, the strain was resuspended in 1 ml of PBS. Next, 1 µg/ml of coelenterazine diluted in ethanol as a substrate was added to the resuspended strain, and then the luciferase activity value in the strain was measured for an exposure time of 1 second using NightOWL II LB 983 In Vivo imaging system (Berthold technologies, GmbH & Co. KG, Germany) or Biorad Imager ChemoDoc™ XRS+ system. The measured value was normalized by the CFU of each strain, and the normalized value was calculated as relative luminescence units (RLU) using the value obtained for the control plasmid not containing Rluc8. The results are shown in FIGS. 5 and 6.

Figure 5:
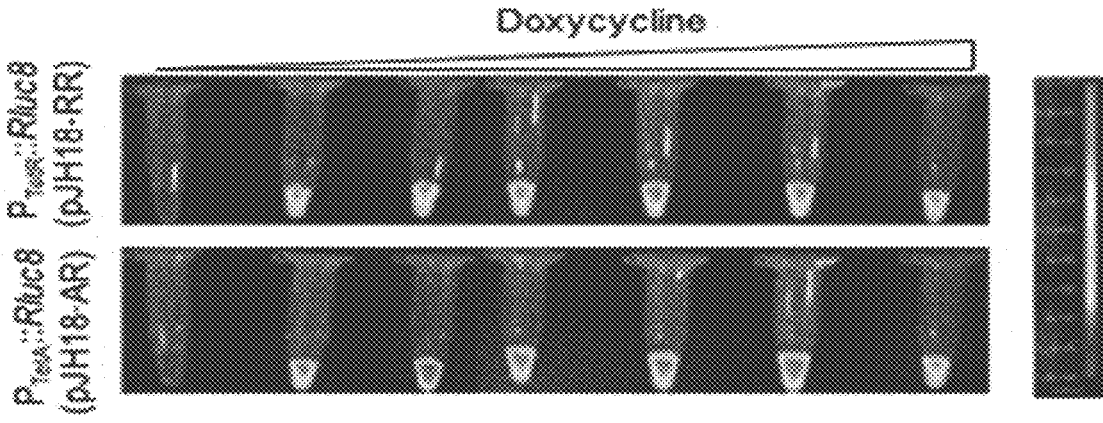
Figure 6:
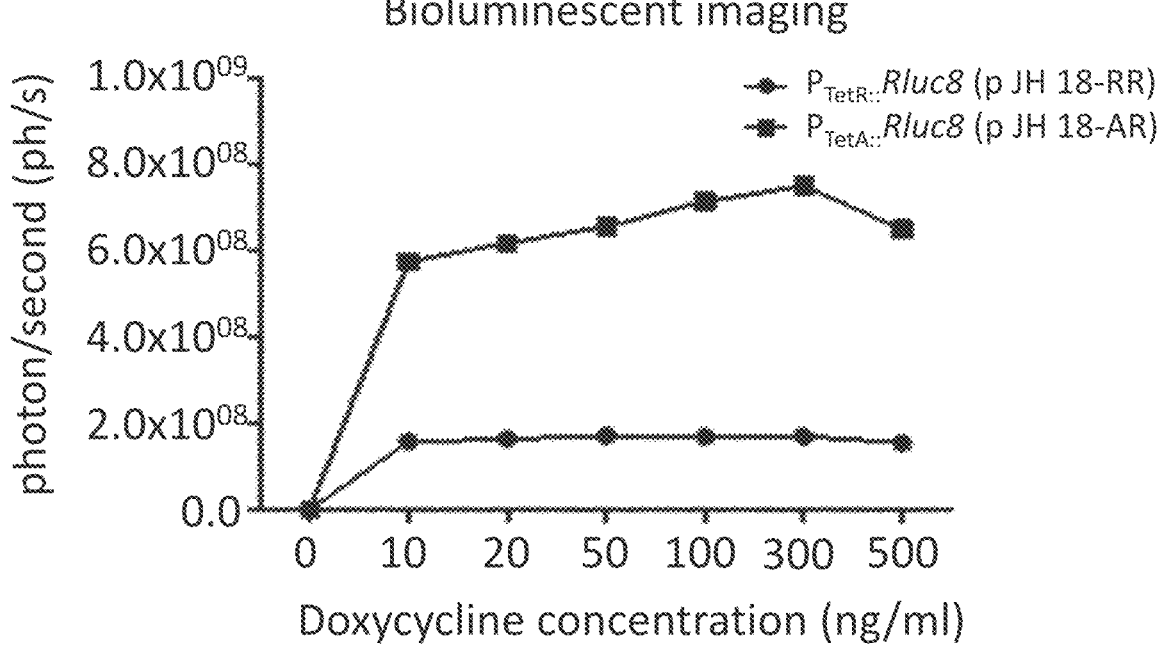

As shown in FIGS. 5 and 6, it was confirmed that the luciferase activity value was found only in the presence of doxycycline (FIG. 5), and the activity level of the protein regulated by the tetA promoter was about three times higher than the activity level of the protein regulated by the tetR promoter (FIG. 6).

From the above results, it can be seen that, when the tetR protein, which is a regulatory protein capable of suppressing the tetA promoter and the tetR promoter, is continuously expressed by a separate promoter, the tetA promoter and the tetR promoter can be simultaneously induced only in the presence of an inhibitor of the tetR protein.

[2-3] Comparison of Luciferase Activity between DTetII Plasmid and pJH18-CR Plasmid The pTetII plasmid and pJH18-CR plasmid prepared as intermediate products in Preparation Example [1-1] were each introduced into the strain in the same manner as in Preparation Example 3, and then the luciferase activity in each of the strains was measured in the same manner as in Example [2-2]. The results of the measurement are shown in FIGS. 7 and 8.

Figure 7:
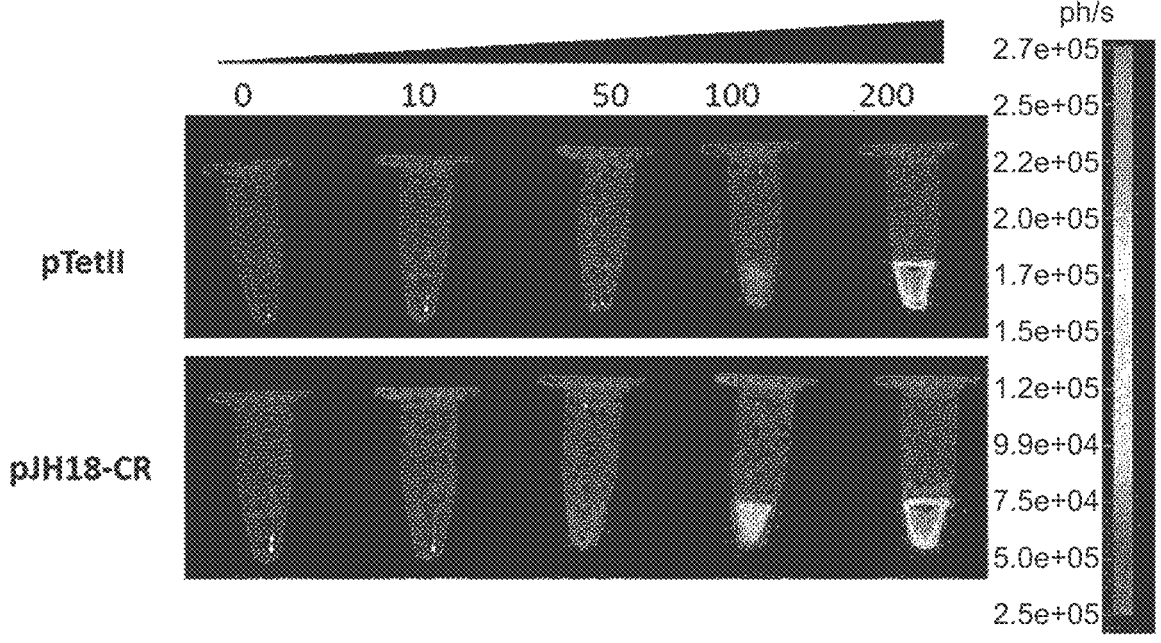
FIGS. 7 and 8 show the results of analyzing the luciferase activity of a reporter protein according to one embodiment of the present disclosure.
Figure 8:
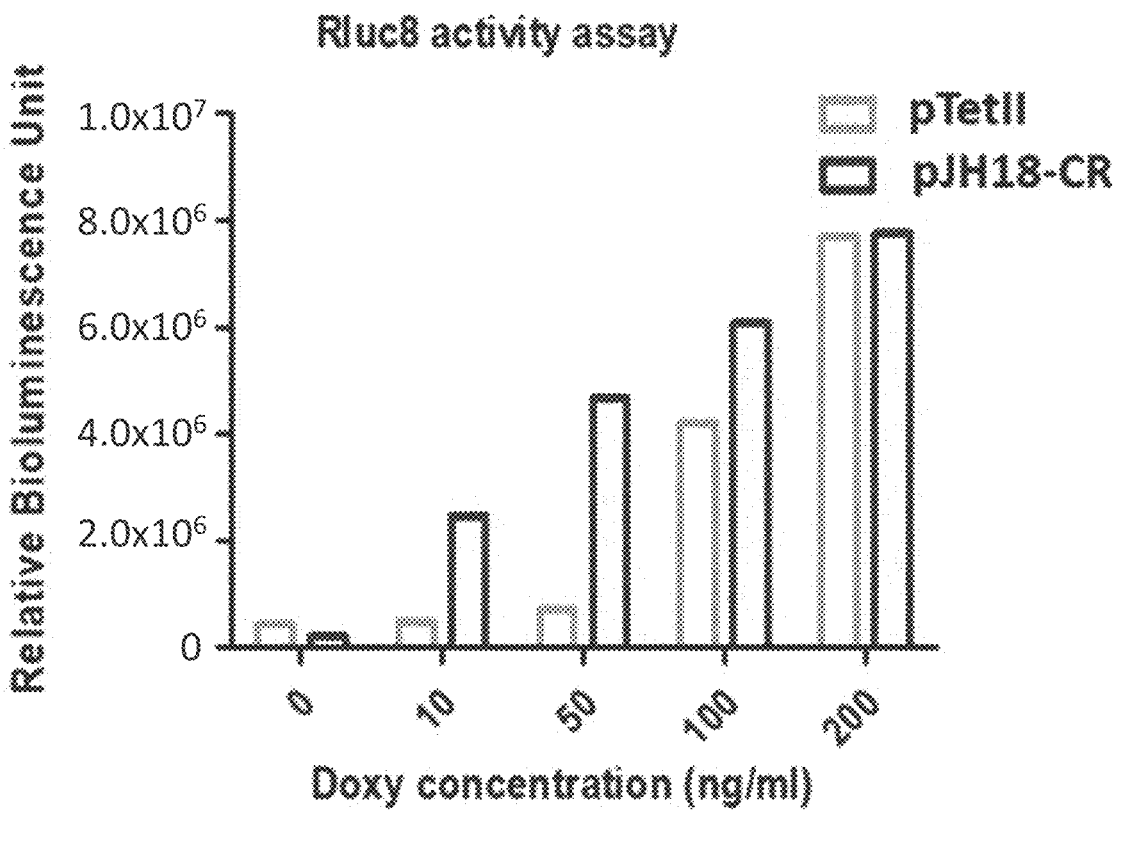

As shown in FIGS. 7 and 8, it was confirmed that the luciferase activity value increased depending on the concentration of doxycycline, not only in the presence of the OXB1 promoter (pJH118-CR), but also in the case in which the nucleotide sequences represented by SEQ ID NO: 8 and SEQ ID NO: 9 were located at the −35 site and the −10 site, respectively.

From the above results, it can be seen that the plasmid containing the DNA construct according to the present disclosure can continuously express the regulatory protein, even when a separate promoter is not artificially introduced upstream of the regulatory protein, because the nucleotide sequences included in the plasmid act as a promoter so that expression of the regulatory protein can be induced.

[2-4] Comparison of Luciferase Activity between DNA Constructs Comprising OXB1 and OXB11 Promoters, Respectively The pTetOXB11 plasmid and pJH18 plasmid prepared in Preparation Example [1-2] were each introduced into the strain in the same manner as in Preparation Example 3, and then the luciferase activity in each of the strains was measured in the same manner as in Example [2-2] above. The results of the measurement are shown in FIGS. 9 and 10.

Figure 9:
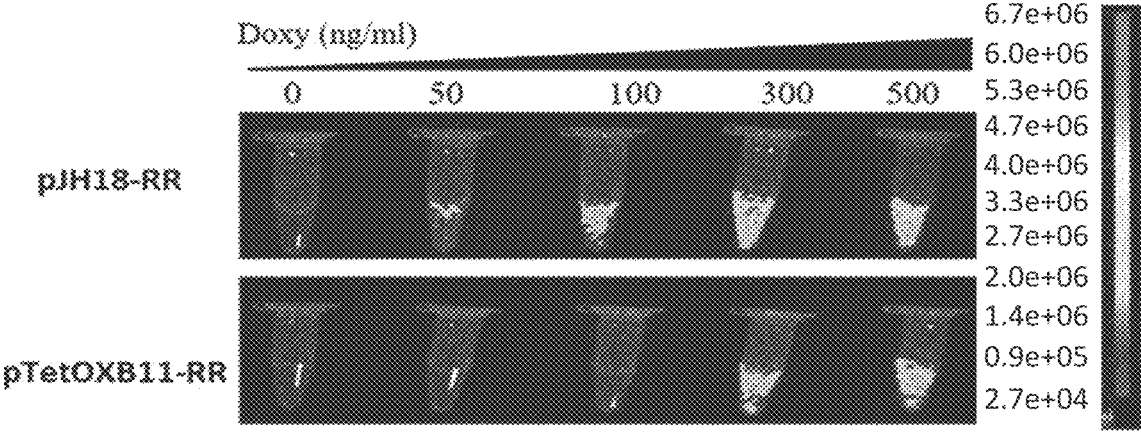
FIGS. 9 and 10 show the results of analyzing the luciferase activity of a reporter protein according to one embodiment of the present disclosure.
Figure 10:
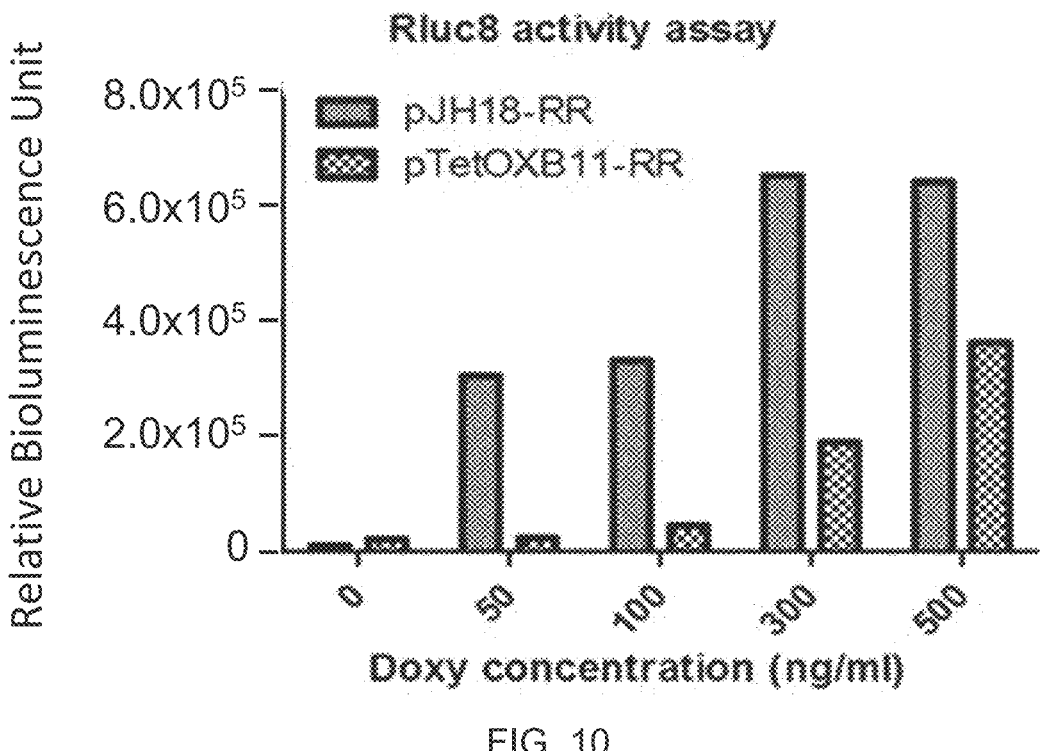

As shown in FIGS. 9 and 10, it was confirmed that the luciferase activity was higher in the presence of the OXB1 promoter (pJH18), which is a weak promoter, than in the presence of the OXB11 promoter (pTetOXB11).

From the above results, it can be seen that, as compared to the plasmid comprising the intermediate promoter, the plasmid comprising the weak promoter allows the regulatory protein present downstream of the promoter to be expressed at a low level so that the expression level can be sensitive to the concentration of doxycycline, thereby effectively increasing the expression level of the target protein, and ultimately the expression levels of the genes present downstream of the tetA and tetR promoters are balanced with each other.

[Example 3] Comparison of Protein Expression and Active Levels in Strain Having PJH18-CR Plasmid Introduced Therein

[3-1] Comparison of Protein Expression and Activity Levels

Figure 11:
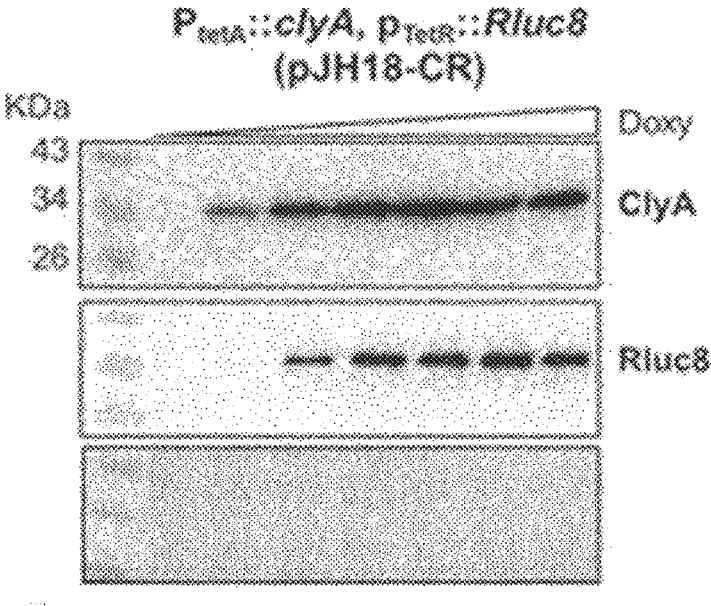
FIG. 11 shows the results of performing Western blot analysis and Coomassie blue staining according to one embodiment of the present disclosure.
Figure 12:
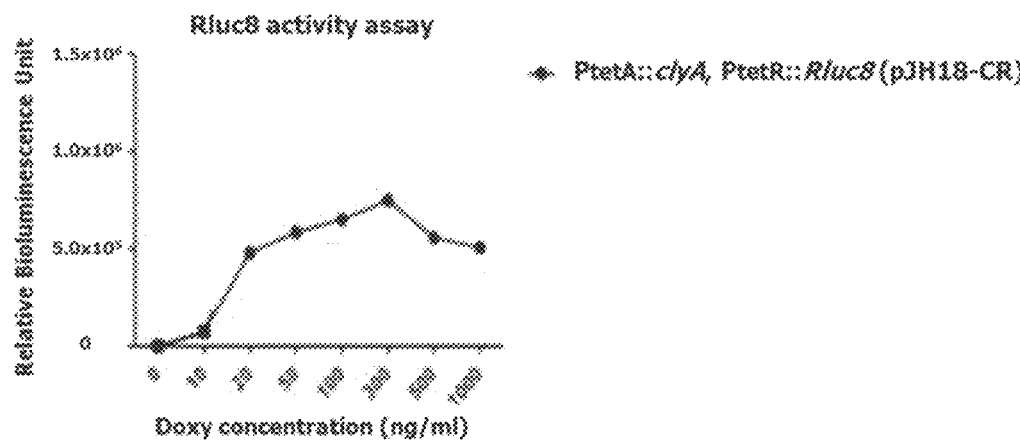
FIG. 12 shows the result of analyzing the expression level of a reporter protein by luciferase activity assay.

According to the same methods as the Western blot analysis, Coomassie blue staining and luciferase activity assay methods described in Examples [2-1] and [2-2] above, analysis of protein expression levels in the strain into which the pJH18-CR($P_{OXB1}$::tetR, $P_{tetA}$::ClyA 및 $P_{tetR}$::Rluc8) of Preparation Example [1-1] has been introduced by the method described in Preparation Example 3 was performed, and the results of the analysis are shown in FIGS. 11 and 12.

As shown in FIGS. 11 and 12, it was confirmed that, when the strain having pJH18-CR introduced therein was treated with doxycycline, the expression level of the cytolysin A protein and the expression level of the Rluc8 protein were almost equally balanced.

[3-2] Analysis of Hemolytic Activity

The strain into which pJH18-CR of Preparation Example [1-1], diluted in PBS, has been introduced by the method described in Preparation Example 3, was plated on a blood agar plate containing 0 or 20 ng/ml doxycycline, and cultured overnight at 37° C., and a photograph of the plate was taken. The photograph is shown in FIG. 13.

Figure 13:
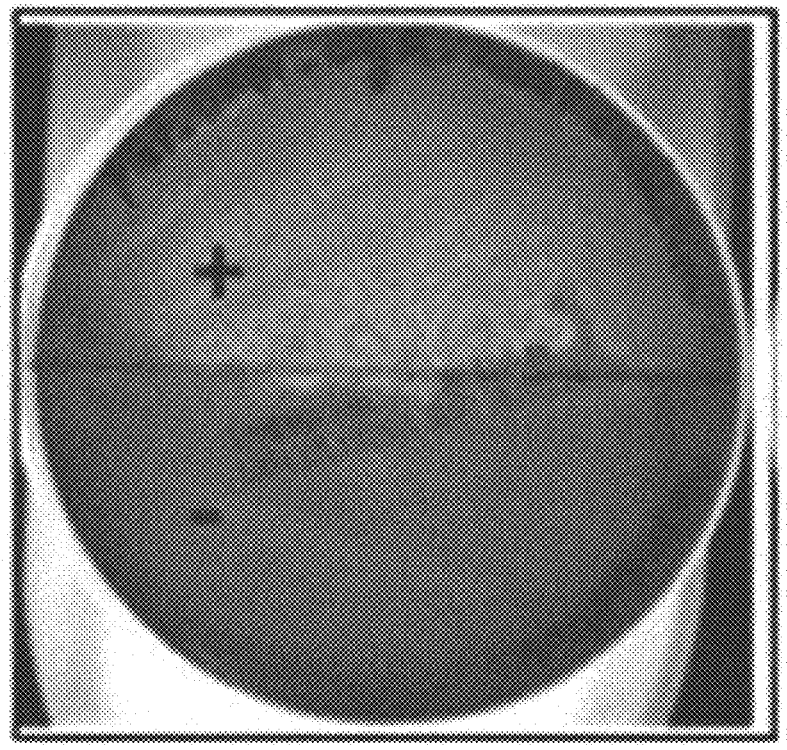
FIG. 13 shows the results of analyzing the degree of hemolytic activity of a strain against blood agar.

As shown in FIG. 13, it was confirmed that the blood agar hemolytic activity of the strain appeared only in the case in which doxycycline was included (+), regardless of the type of promoter present upstream of the gene encoding cytolysin A.

From the above results, it can be seen that the activities of the tetA and tetR promoters of the plasmid according to the present disclosure are induced only by doxycycline, and thus these promoters together can effectively regulate the protein expression level.

[Example 4] Comparison of Protein Expression Levels in Strains Having Each of PJH87 and pJH18-CR Plasmids Introduced Therein According to the same methods as the Western blot analysis, Coomassie blue staining and luciferase activity assay methods described in Examples [2-1] and 12-21 above, analysis of protein expression levels was performed in a state in which the expression level of cytolysin A protein was saturated by administering doxycycline at a concentration of 20 ng/ml or higher to the strains into which each of pJH87 ($P_{tetA}$::ClyA and $P_{tetR}$::TetR::Rluc8) and pJH18-CR ($P_{OXB1}$::tetR, $P_{tetA}$::ClyA and $P_{tetR}$::Rluc8) has been introduced by the method described in Preparation Example 3 above. The results of the analysis are shown in FIGS. 14 to 16.

Figure 14:
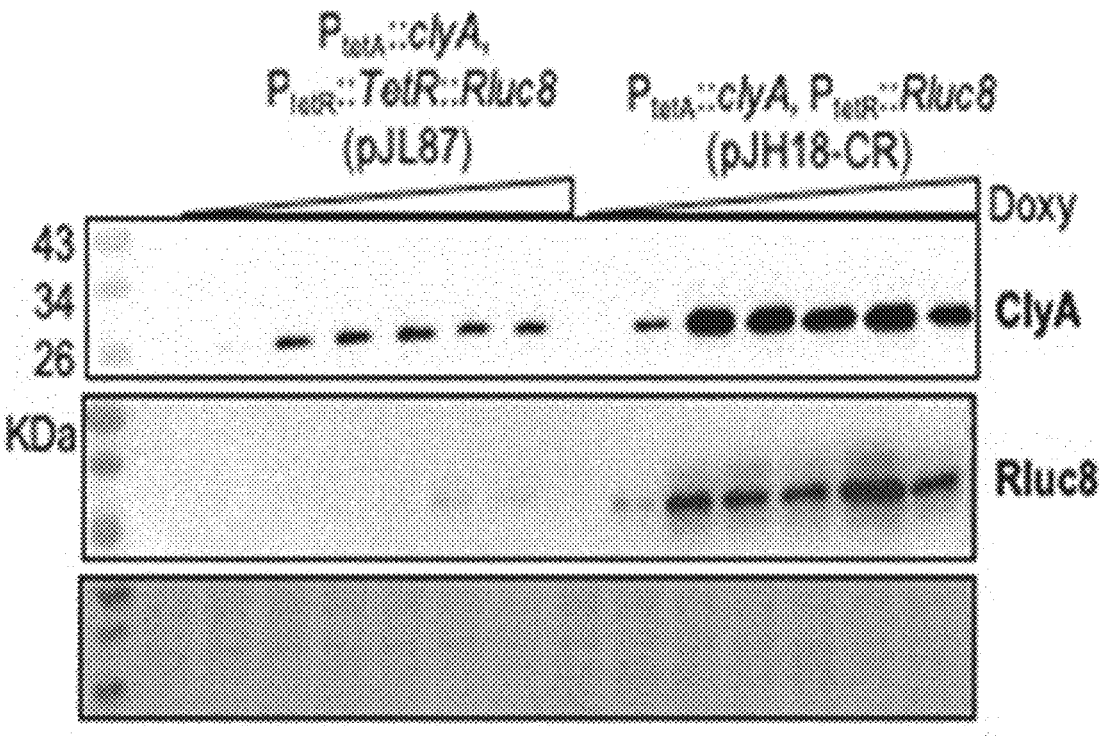
FIG. 14 shows the results of performing Western blot analysis and Coomassie blue staining according to one embodiment of the present disclosure.
Figure 15:
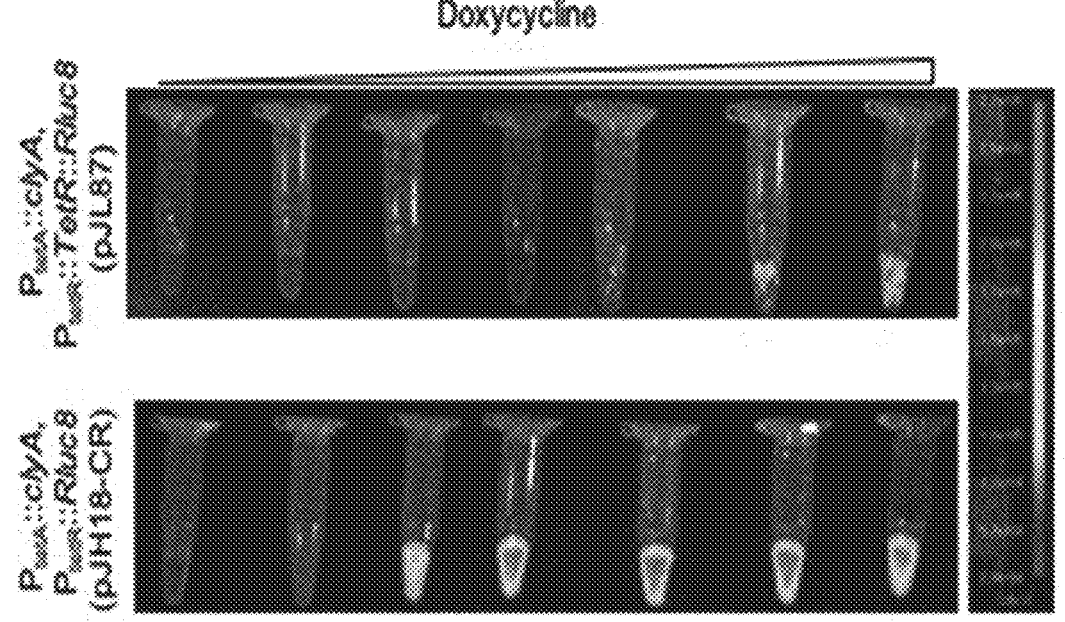
FIGS. 15 and 16 show the results of analyzing the expression level of a reporter protein by luciferase activity assay.
Figure 16:
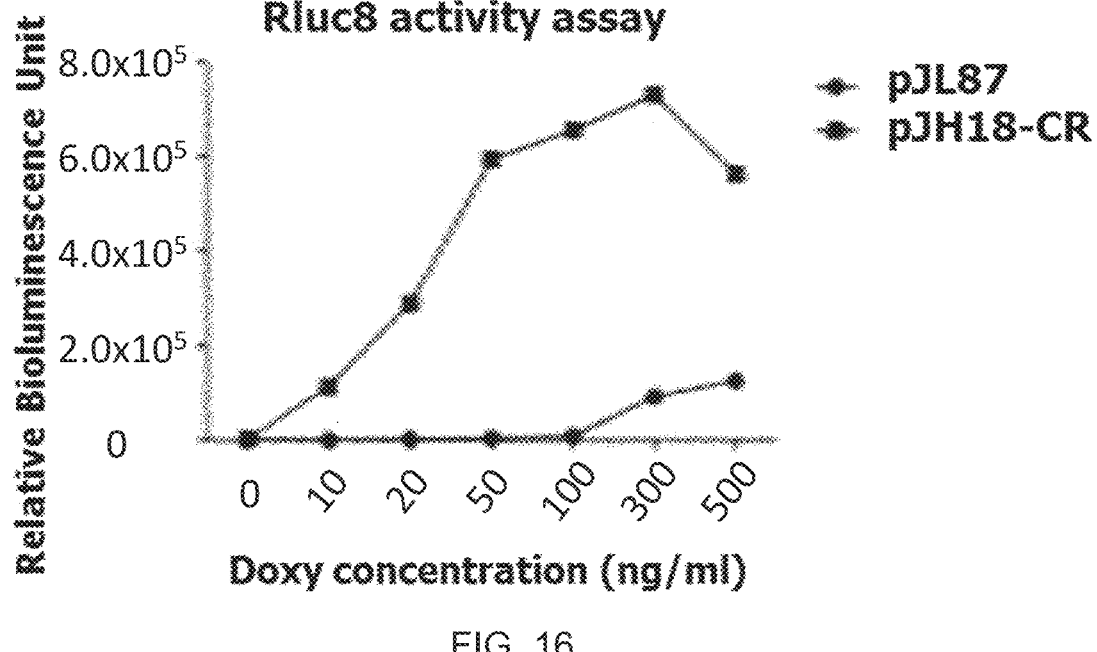

As shown in FIGS. 14 to 16, it was confirmed that the expression level of the cytolysin A protein in the strain having the pJH18-CR plasmid introduced therein was about 5 times higher than that in the strain having the pJH87 plasmid introduced therein. Furthermore, it was confirmed that the activity level of the Rluc8 protein in the strain having the pJH18-CR plasmid introduced therein was about 80 times higher than that the strain having the pJH87 plasmid introduced therein.

From the above results, it can be seen that, as compared to the plasmid configured such that the gene encoding tetR is present downstream of the tetR promoter, in the case in which the gene encoding tetR can be regulated by a separate promoter, particularly, a weak promoter, as described in the present disclosure, the expressions and activities of the anticancer protein and the reporter gene can be induced at high levels by the tetA and tetR promoters whose activities can be induced by a single regulator, and the expression and activities thereof can be relatively balanced.

[Example 5] Tumor Suppression Ability Analysis and Imaging Analysis of Recombinant Strain in Tumor Animal Model with Developed Cancer The *Salmonella* strain, into which pJH18-CR or pJH18 has been introduced by the method described in Preparation Example 3 above, was injected into the tail vein of each tumor animal model constructed in Preparation Example 4 above. Thereafter, according to the luciferase activity assay and Western blot analysis methods described in Examples 12-11 and 12-21, imaging of the strain in the tumor animal model and analysis of the expression level of cytolysin A protein therein were performed, and the results are shown in FIGS. 17 to 19.

Figure 20:
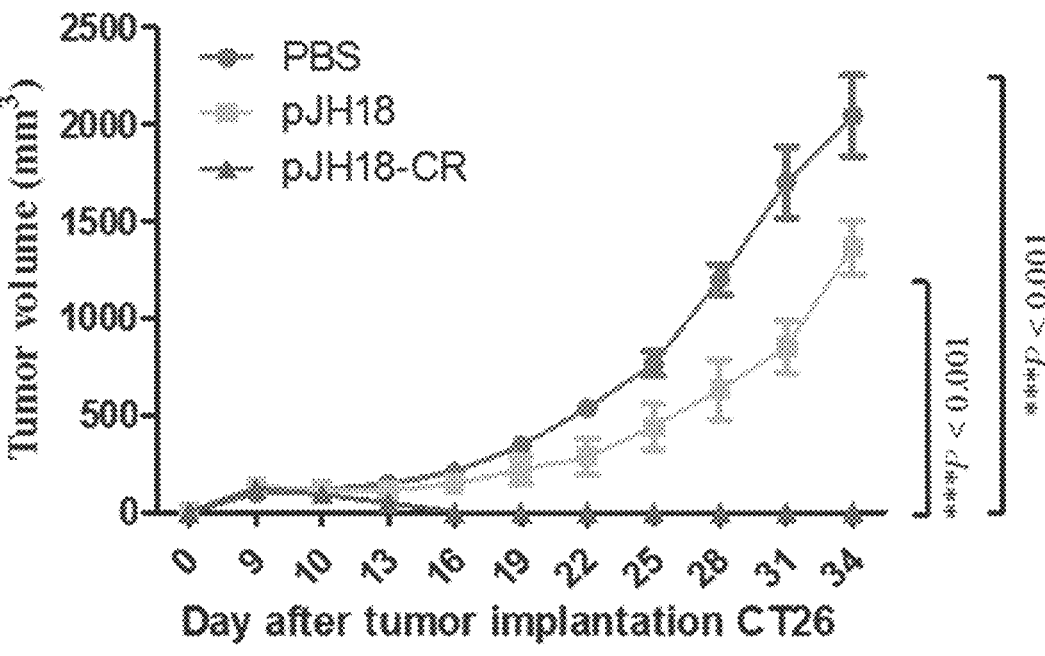
FIG. 20 shows the results of evaluating the tumor volume according to one embodiment of the present disclosure.
Figure 21:
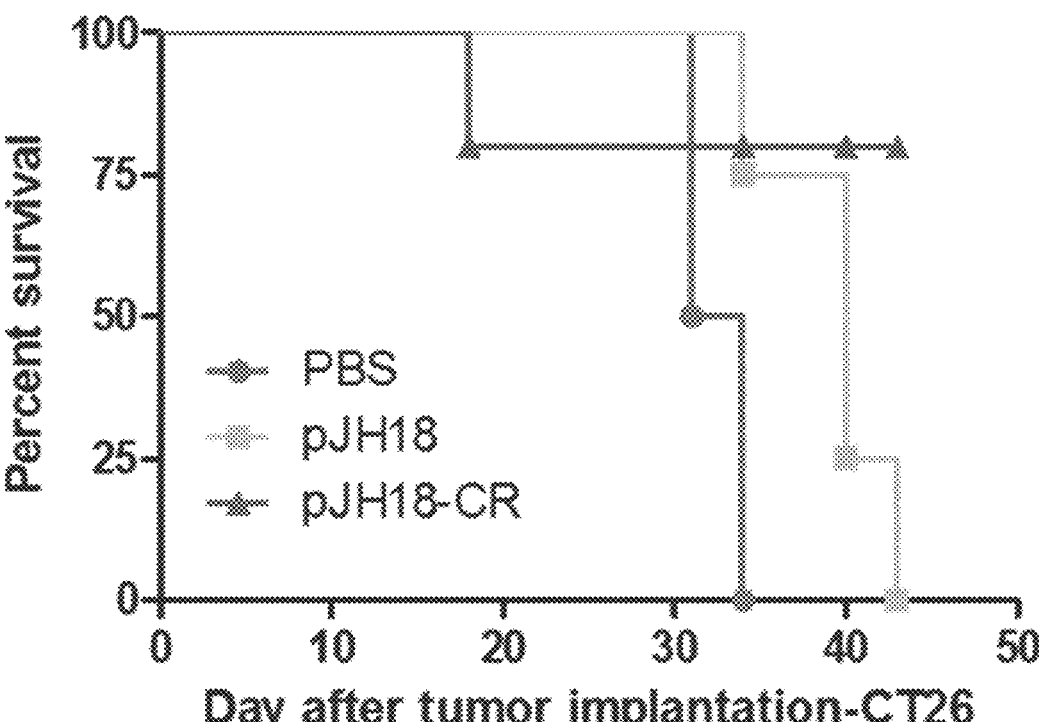
FIG. 21 shows the results of analyzing the survival rate in tumor animal models treated with the strain according to the present disclosure.

In addition, as described in Preparation Example 4, the volume of the tumor in each tumor animal model was measured for 0 to 34 days, and the survival rate of the tumor animal models was measured for 50 days. The results of the measurements are shown in FIGS. 20 and 21. Here, as a control, only PBS was injected into the tail vein of the tumor animal model.

Figure 17:
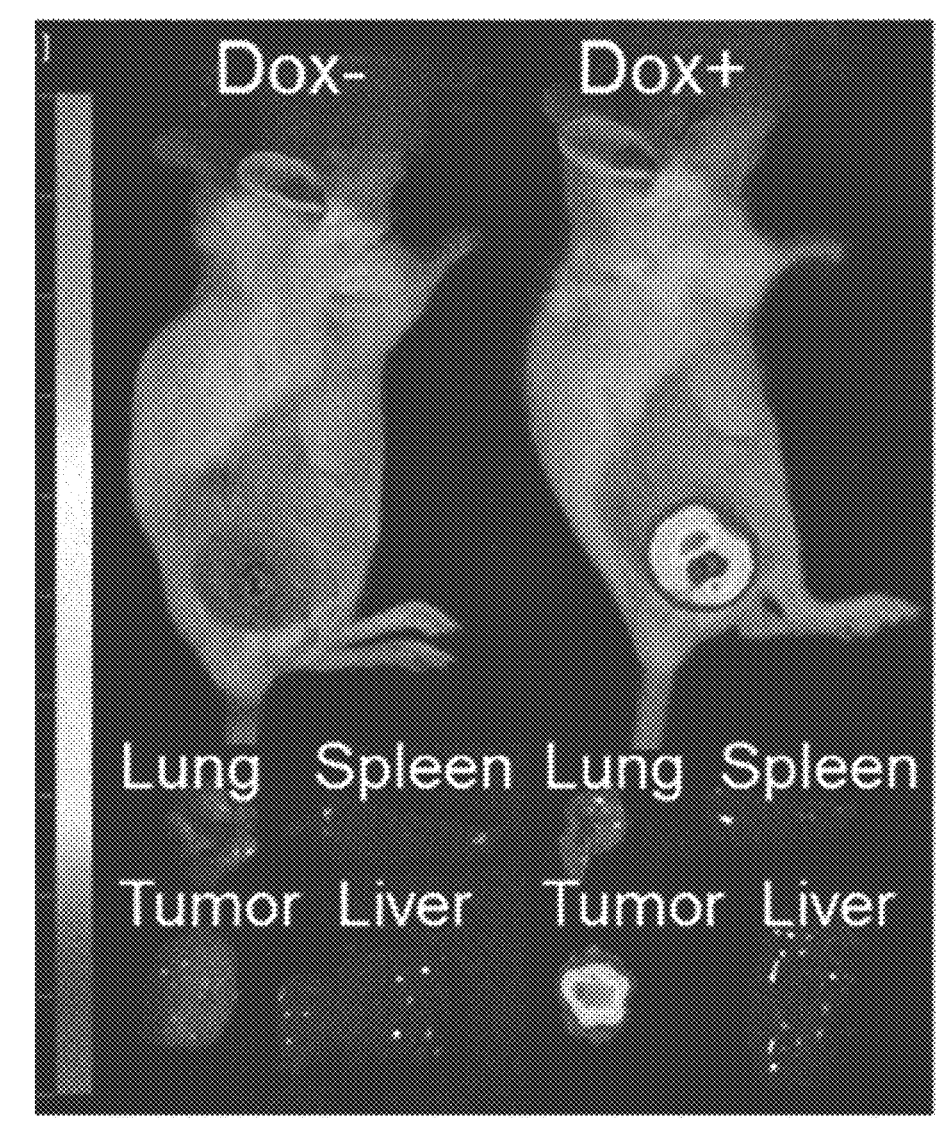
FIGS. 17 and 18 show the results of analyzing the expression level of a reporter protein in a tumor animal model by luciferase activity assay according to one embodiment of the present disclosure.
Figure 18:
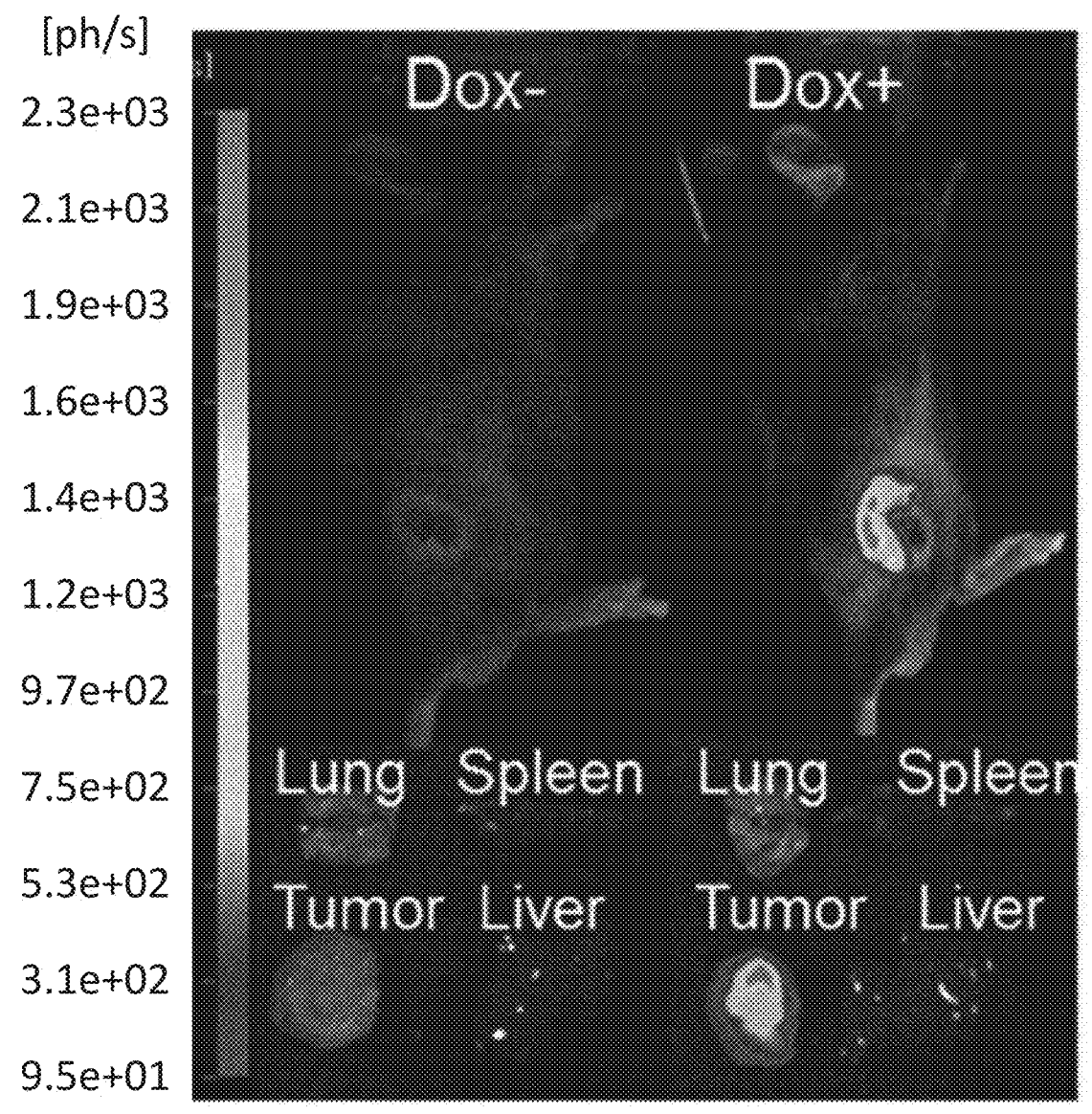
Figure 19:
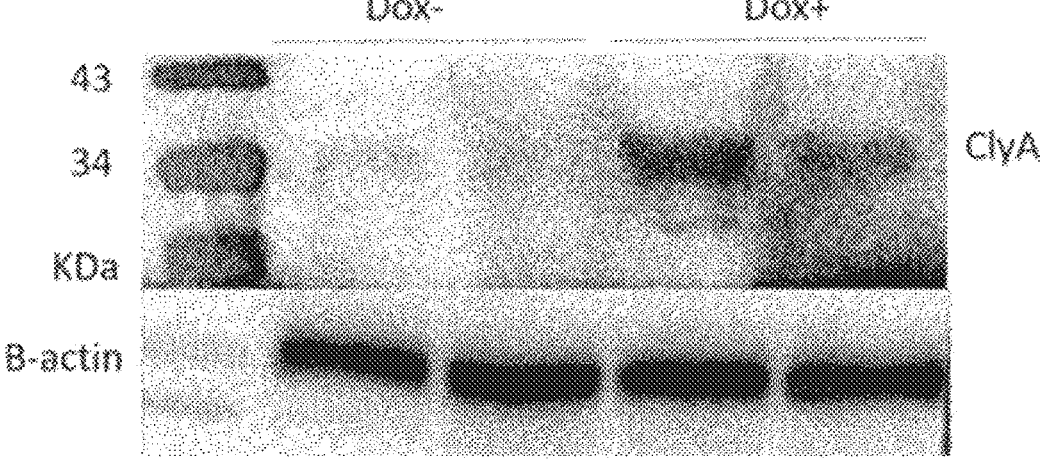
FIG. 19 shows the results of analyzing the expression level of cytolysin A (ClyA) protein in tumor tissue by Western blot analysis.

As shown in FIGS. 17 to 18, it was confirmed that luciferase activity was found only in the tumor tissue of the tumor animal model injected with the *Salmonella* strain having pJH18-CR introduced therein, compared to the control. Furthermore, it was confirmed that luciferase activity was found even when the tumor tissue was extracted from the tumor animal model injected with the *Salmonella* strain having pJH18-CR introduced therein. In addition, as shown in FIG. 19, it was confirmed that, in the case of the *Salmonella* strain having pJH18-CR introduced therein, the cytolysin A protein was specifically expressed only in the presence of doxycycline (Dox+).

As shown in FIGS. 20 and 21, it was confirmed that the tumor volume significantly decreased in the tumor animal models in which the cytolysin A protein was expressed from the *Salmonella* strain having pJH18-CR introduced therein, compared to the case in which PBS or pJH18 was injected, and the survival rate of these tumor animal models increased.

From the above results, it can be seen that, in the case of the *Salmonella* strain into which pJH18-CR according to the present disclosure has been introduced, the promoters that regulate the expression levels of the imageable protein and the anticancer protein can be activated by the single regulatory protein, suggesting that the strain enables accurate imaging of the location of a tumor in an individual with a developed tumor, and at the same time, can significantly improve the survival rate of individuals with developed cancer by suppressing the growth of a tumor.

[Example 6] Comparison of Luciferase Activity Between DNA Constructs

Comprising Promoters

Each of the pTetTac-RR, pTetJ23101-RR and pTetJ23119-RR plasmids constructed in Preparation Examples [1-3] to [1-5] was introduced into the strain in the same manner as in Preparation Example 3, and the luciferase activity in each of the strains was measured in the same manner as in Example [2-2]. The results of the measurement are shown in FIGS. 22 and 23.

Figure 22:
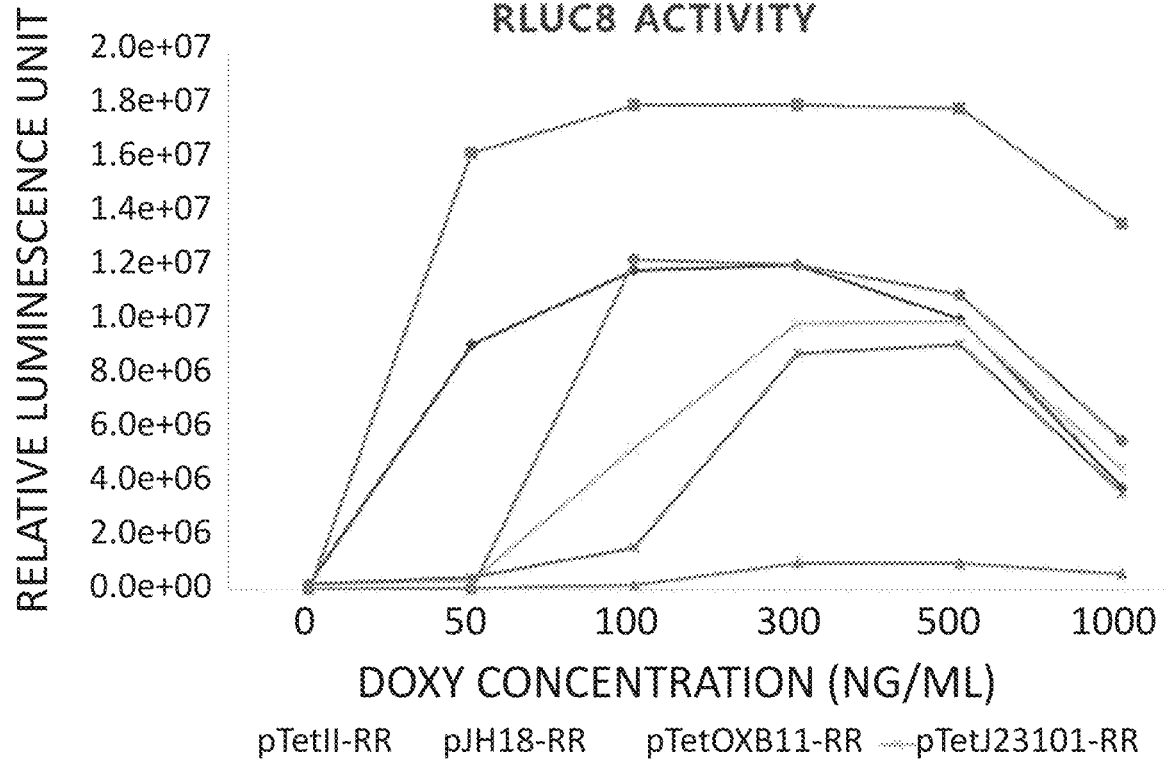
FIG. 22 graphically shows the luciferase activities in strains into which pTetTac-RR, pTetJ23101-RR and pTetJ23119-RR plasmids according to one embodiment of the present disclosure have been introduced.
Figure 23:
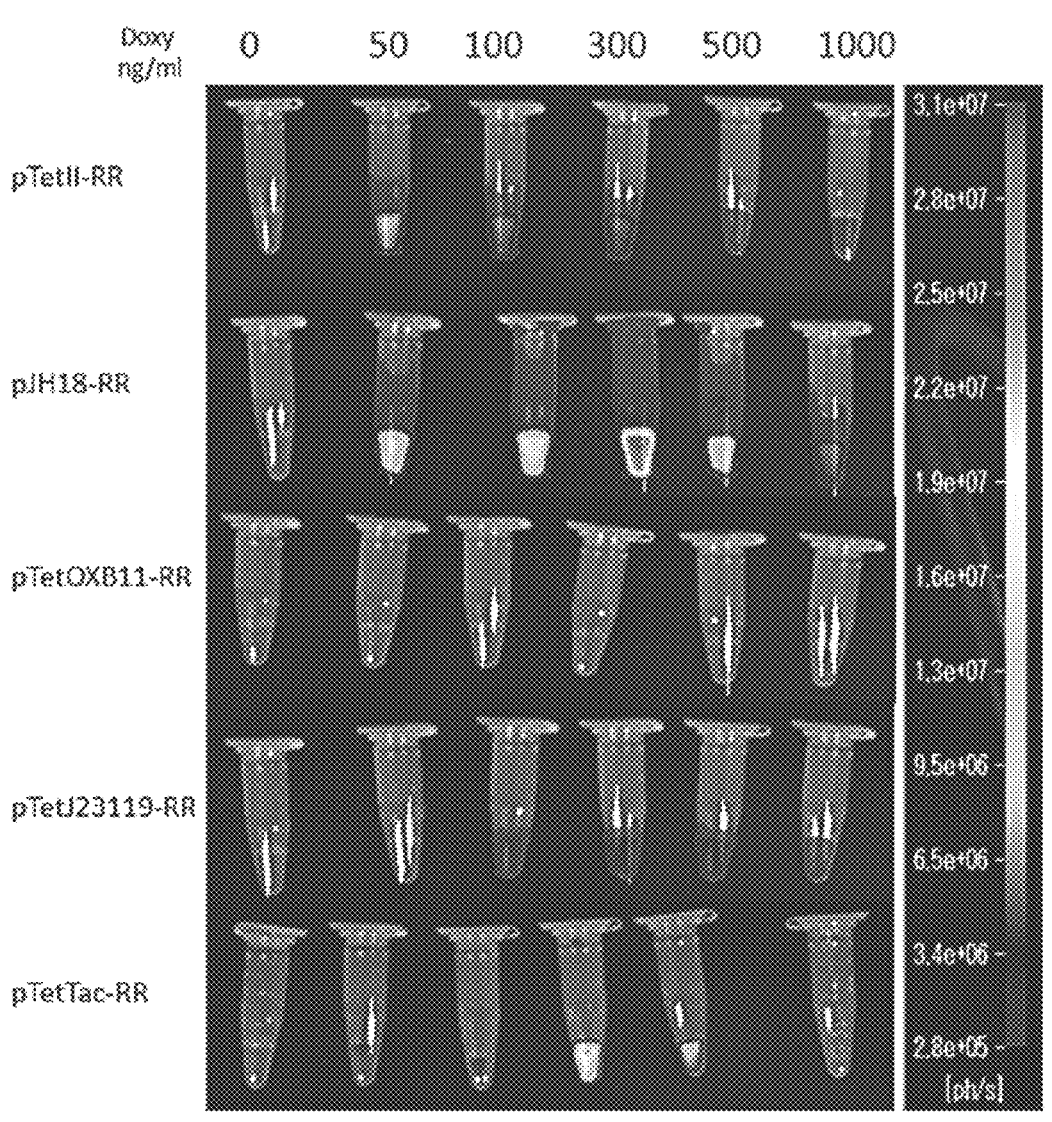
FIG. 23 shows the luciferase activities in strains into which pTetTac-RR, pTetJ23101-RR and pTetJ23119-RR plasmids according to one embodiment of the present disclosure have been introduced.

As shown in FIGS. 22 and 23, it was confirmed that, in the case of the plasmid (pJH18) containing the OXB1 promoter, sensitivity to doxycycline and luciferase activity were higher than in the case of the plasmids (pTetTac-RR, pTetJ23101-RR, and pTetJ23119-RR) containing the Tac, J23101 and J23119 promoters, respectively.

From the above results, it can be seen that, as compared to the plasmid comprising the published constitutive promoter, the plasmid comprising the weak promoter according to the present disclosure allows the regulatory protein present downstream of the promoters thereof to be expressed at a low level so that the expression level can be sensitive to the concentration of doxycycline, thereby effectively increasing the expression level of the target protein, and ultimately the expression levels of the genes present downstream of the tetA and tetR promoters are balanced with each other.

Although the present disclosure has been described in detail with reference to the specific features, it will be apparent to those skilled in the art that this description is only of a preferred embodiment thereof, and does not limit the scope of the present disclosure. Thus, the substantial scope of the present disclosure will be defined by the appended claims and equivalents thereto.

INDUSTRIAL APPLICABILITY

The present disclosure relates to a DNA construct for diagnosing and treating cancer and a strain into which a recombinant vector comprising the DNA construct has been introduced.

Sequence List Free Text
SEQ ID NO 1: Cytolysin A amino acid sequence
10        20        30        40        50
MIMTGIFAEQ TVEVVKSAIE TADGALDLYN KYLDQVIPWK

TFDETIKELS 60        70        80        90        100
RFKQEYSQEA SVLVGDIKVL LMDSQDKYFE ATQTVYEWCG

VVTQLLSAYI 110       120       130       140       150
LLFDEYNEKK ASAQKDILIR ILDDGVKKLN EAQKSLLTSS

QSFNNASGKL 160       170       180       190       200
LALDSQLTND FSEKSSYFQS QVDRIRKEAY AGAAAGIVAG

PFGLIISYSI 210       220       230       240       250
AAGVIEGKLI PELNNRLKTV QNFFTSLSAT VKQANKDIDA

AKLKLATEIA 260       270       280       290       300
AIGEIKTETE TTRFYVDYDD LMLSLLKGAA KKMINTCNEY

QQRHGKKTLF

EVPDV

SEQ ID NO 2: Forward primer
5'-CGGAATTCACCATGTCTAGATTAGATAAAAGTAAAGTGATTAACAG-

3'

-continued

-continued

SEQ ID NO 3: Reverse primer
5'-GCTCTAGACAGCTGTTAAGACCCACTTTCACATTTAAGTTGTTTTTC

T-3'

SEQ ID NO 4: Forward primer
5'-CTACTCCGTCAAGCCGTCAAGCTGTTGTGACCGCTTGCT-3'

SEQ ID NO 5: Reverse primer
5'-TGAATTCCTCCTGCTAGCTAGTTGGTAACGAATCAGACGCCGGGTAAT

ACCGGATAG-3'

SEQ ID NO 6: Forward primer
5'-TGCTACTCCGTCAAGCCGTCAAGCTGTTGTGACCGCTTG-3'

SEQ ID NO 7: Reverse primer
5'-AGCTTGGTAACGAATCAGACGCCGGGTAATACCGGATAG-3'

SEQ ID NO 8: -35 promoter
TTCGCG

SEQ ID NO 9: -10 promoter
ATGCATAAT

SEQ ID NO 10: Forward primer
5'-CCCTATGCTACTCCGTCAAGCCGTCAATTGTTGACAATTAATCATCGG

CTCGTATAATGTCTGATTCGTTACCAAGCT-3'

SEQ ID NO 11: Reverse primer
5'-AGCTTGGTAACGAATCAGACATTATACGAGCCGATGATTAATTGTCAA

CAATTGACGGCTTGACGGAGTAGCATAGG-G-3'

SEQ ID NO 12: Forward primer
5'-TGCTACTCCGTCAAGCCGTCTTTACAGCTAGCTCAGTCCTAGGTATAA

TGCTAGCCAATTGTCTGATTCGTTACC-3'

SEQ ID NO 13: Reverse primer
5'-GGTAACGAATCAGACAATTGGCTAGCATTATACCTAGGACTGAGCTAG

CTGTAAAGACGGCTTGACGGAGTAGCA-3'

SEQ ID NO 14: Forward primer
5'-TGCTACTCCGTCAAGCCGTCTTGACAGCTAGCTCAGTCCTAGGTATAA

TGCTAGCCAATTGTCTGATTCGTTACC-3'

SEQ ID NO 15: Reverse primer
5'-GGTAACGAATCAGACAATTGGCTAGCATTATACCTAGGACTGAGCTAG

CTGTCAAGACGGCTTGACGGAGTAGCA-3'

SEQ ID NO 16: OX131 promoter
5'-AAGCTGTTGTGACCGCTTGCTCTAGCCAGCTATCGAGTTGTGAACCGA

TCCATCTAGCAATTGGTCTCGATCTAGCGATAGGCTTCGATCTAGCTATGT

AGAAACGCCGTGTGCTCGATCGCCTGACGCTTTTTATCGCAACTCTCTACT

GTTGCTTCAACAGAACATATTGACTATCCGGTATTACCCGGC-3'

The invention claimed is:

1. A DNA construct comprising
a gene encoding a regulatory protein;
a promoter of the gene encoding the regulatory protein;
a first promoter and a second promoter, each induced by the regulatory protein; and
at least one selected from the group consisting of a gene encoding an anticancer protein, a gene encoding a cytokine, a gene encoding a chemokine, a gene encoding an immune modulator, a cancer antigen-specific oligonucleotide, and a gene encoding a reporter protein,
wherein the regulatory protein is a TetR protein,
wherein the promoter of the gene encoding the regulatory protein is a OXB1 promoter
wherein the first promoter is a tetA promoter, and the second promoter is a tetR promoter, and wherein any one selected from the group consisting of the gene encoding an anticancer protein, the gene encoding a cytokine, the gene encoding a chemokine, the gene encoding an immune modulator, the cancer antigen-specific oligonucleotide, and the gene encoding a reporter protein is operably linked downstream of the first promoter and the second promoter.

2. The DNA construct of claim 1, wherein the anticancer protein is at least one selected from the group consisting of a toxin protein, an antibody specific for a cancer antigen or a fragment of the antibody, a tumor suppressor protein, an angiogenesis inhibitor, a cancer antigen, a prodrug-converting enzyme, and a pro-apoptotic protein.

3. The DNA construct of claim 2, wherein the anticancer protein is the toxin protein, and the toxin protein is at least one selected from the group consisting of ricin, saporin, gelonin, momordin, debouganin, diphtheria toxin, Pseudomonas toxin, hemolysin (HlyA), FAS ligand (FASL), tumor necrosis factor-α (TNF-α), TNF-related apoptosis-inducing ligand (TRAIL), and cytolysin A (ClyA).

4. The DNA construct of claim 2, wherein the anticancer protein is the tumor suppressor protein, and the tumor suppressor protein is at least one selected from the group consisting of retinoblastoma (RB) protein, p53 protein, adenomatous polyposis coli (APC) protein, phosphatase and tensin homologue (PTEN) protein, cyclin dependent kinase inhibitor 2A (CDKN2A) protein.

5. The DNA construct of claim 2, wherein the anticancer protein is the angiogenesis inhibitor protein, and the angiogenesis inhibitor is at least one selected from the group consisting of angiostatin, endostatin, thrombospondin, and protease inhibitory proteins.

6. The DNA construct of claim 2, wherein the anticancer protein is the cancer antigen, and the cancer antigen is at least one selected from the group consisting of α-fetoprotein (AFP), vascular endothelial growth factor receptor 2 (VEGFR2), Survivin, Legumain, prostate cancer-specific antigen (PCSA).

7. The DNA construct of claim 2, wherein the anticancer protein is the prodrug converting enzyme, and the prodrug converting enzyme is at least one selected from the group consisting of thymidine kinase, cytosine deaminase, nitroreductase, purine nucleoside phosphorylase, carboxypeptidase G2, chromate reductase YieF, herpes simplex virus type I thymidine kinase/ganciclovir (HSV1-TK/GCV), and β-glucuronidase.

8. The DNA construct of claim 2, wherein the anticancer protein is the pro-apoptotic protein, and the pro-apoptotic protein is L-ASNase or RNA-binding motif protein 5 (RBM5).

9. The DNA construct of claim 1, wherein the DNA construct comprises the gene encoding the cancer antigen-specific oligonucleotide, the gene encoding the cancer antigen-specific oligonucleotide is operatively linked downstream of the first promoter and the second promoter, and the cancer antigen-specific oligonucleotide is a nucleotide sequence encoding at least one selected from the group consisting of an antisense oligonucleotide, an aptamer, siRNA, and shRN.

10. The DNA construct of claim 1, wherein the DNA construct comprises the gene encoding the reporter protein, the gene encoding the reporter protein is operatively linked downstream of the first promoter and the second promoter, and the reporter protein is at least one selected from the group consisting of a fluorescent protein, luciferase, and a protein which is used in nuclear medicine or MRI imaging.

11. The DNA construct of claim 10, wherein the reporter protein is the fluorescent protein that is at least one selected from the group consisting of green fluorescent protein (GFP), modified green fluorescent protein (MGFP), enhanced green fluorescent protein (EGFP), red fluorescent protein (RFP), enhanced red fluorescent protein (ERFP), blue fluorescent protein (BFP), enhanced blue fluorescent protein (EBFP), yellow fluorescent protein (YFP), and enhanced yellow fluorescent protein (EYFP).

12. The DNA construct of claim 10, wherein the reporter protein is the protein which is used in nuclear medicine or MRI imaging that is at least one selected from the group consisting of herpes simplex virus thymidine kinase, dopamine receptor, somatostatin receptor, sodium-iodide transporter, iron receptor, transferrin receptor, ferritin and iron transporter (magA).

13. A recombinant vector comprising the DNA construct of claim 1.

14. A strain into which the recombinant vector of claim 13 has been introduced.

15. A method for preventing or treating cancer, the method comprising a step of administering to a subject a pharmaceutically effective amount of the strain of claim 14.

* * * * *